(12) United States Patent
Edwards et al.

(10) Patent No.: US 9,332,796 B2
(45) Date of Patent: May 10, 2016

(54) CLOTHING TOP FOR TECHNOLOGY CONCEALMENT

(71) Applicant: Mile High Hoodies, LLC, Aurora, CO (US)

(72) Inventors: Elvis Edwards, Aurora, CO (US); Marietta Cantu, Aurora, CO (US); Chad J. Cantu, Aurora, CO (US)

(73) Assignee: MILE HIGH HOODIES, LLC, Aurora, CO (US)

( * ) Notice: Subject to any disclaimer, the term of this patent is extended or adjusted under 35 U.S.C. 154(b) by 0 days.

(21) Appl. No.: 14/801,451

(22) Filed: Jul. 16, 2015

(65) Prior Publication Data

US 2016/0015104 A1    Jan. 21, 2016

Related U.S. Application Data

(60) Provisional application No. 62/025,829, filed on Jul. 17, 2014.

(51) Int. Cl.
| | | |
|---|---|---|
| *A41D 27/20* | (2006.01) | |
| *A41D 1/00* | (2006.01) | |
| *A41D 1/02* | (2006.01) | |
| *A41D 13/00* | (2006.01) | |

(52) U.S. Cl.
CPC ............... *A41D 27/20* (2013.01); *A41D 1/002* (2013.01); *A41D 1/02* (2013.01); *A41D 13/0012* (2013.01); *A41D 2200/20* (2013.01)

(58) Field of Classification Search
CPC ...... A41D 13/0012; A41D 1/04; A41D 20/00; A41D 13/0512; A41D 27/20; A41D 13/018; A41D 3/00; A42B 1/046

USPC ............ 2/94, 102, 170, 468, 202, 247, 456, 2/2.11, 108, DIG. 3
See application file for complete search history.

(56) References Cited

U.S. PATENT DOCUMENTS

| | | | |
|---|---|---|---|
| 1,900,129 A | 3/1933 | Ring | |
| 2,078,844 A | 4/1937 | Gardian | |
| 2,426,726 A * | 9/1947 | Combs | A41D 7/003 441/102 |
| 4,070,553 A * | 1/1978 | Hass | H04M 1/05 381/151 |
| 4,243,058 A | 1/1981 | Gershbein | |
| 4,322,585 A | 3/1982 | Liautaud | |
| 4,526,298 A | 7/1985 | Boxer et al. | |

(Continued)

FOREIGN PATENT DOCUMENTS

| | | |
|---|---|---|
| WO | 02/080714 A1 | 10/2002 |
| WO | 2008/025043 A1 | 3/2008 |

OTHER PUBLICATIONS

International Search Report and Written Opinion for PCT/US15/40787 mailed Jan. 12, 2016, 18 pages.

*Primary Examiner* — Tejash Patel
(74) *Attorney, Agent, or Firm* — Kilpatrick Townsend & Stockton LLP

(57) ABSTRACT

Various embodiment of a body-top garment for removably housing a tube assembly is disclosed. The tube assembly has a first end that connects to a mouthpiece, and a second end connects to various types of devices. The body-top garment has an elongated pouch with a zipper opening for easy access to the tube assembly. The elongated pouch has a first opening and a second opening to pass at least part of the tube assembly outside the body-top garment. Optionally, the body-top garment has pocket with a horizontal opening to hold the various type of devices.

19 Claims, 35 Drawing Sheets

(56) References Cited

U.S. PATENT DOCUMENTS

| | | | |
|---|---|---|---|
| 4,589,134 A * | 5/1986 | Waldron | H04R 5/02 |
| | | | 381/301 |
| 4,876,724 A | 10/1989 | Suzuki | |
| 5,400,934 A | 3/1995 | Ducros | |
| 5,416,310 A | 5/1995 | Little | |
| 5,555,490 A | 9/1996 | Carroll | |
| 5,722,573 A * | 3/1998 | Carnel | A45F 3/16 |
| | | | 224/148.2 |
| 5,816,457 A | 10/1998 | Croft | |
| 6,339,846 B2 | 1/2002 | Uchida | |
| 6,801,140 B2 | 10/2004 | Mantyjarvi et al. | |
| 6,826,782 B2 | 12/2004 | Jordan | |
| 7,168,098 B2 | 1/2007 | West | |
| 7,265,970 B2 | 9/2007 | Jordan | |
| 7,302,710 B2 * | 12/2007 | Thomas | A41D 1/04 |
| | | | 2/84 |
| RE40,613 E | 1/2009 | Jordan | |
| 7,519,192 B1 | 4/2009 | Laycock et al. | |
| 7,673,348 B2 * | 3/2010 | Williams | A41D 1/005 |
| | | | 2/115 |
| 7,841,344 B2 * | 11/2010 | Schlosser | A41D 13/018 |
| | | | 128/205.22 |
| 7,992,225 B2 | 8/2011 | Demus | |
| 8,107,653 B2 * | 1/2012 | Wolfe | A41D 1/002 |
| | | | 381/301 |
| 8,549,670 B2 | 10/2013 | Demus | |
| 8,613,112 B2 | 12/2013 | Santucci et al. | |
| 8,687,834 B2 * | 4/2014 | Wolfe | H04R 1/028 |
| | | | 381/301 |
| 8,756,716 B2 | 6/2014 | Jordan et al. | |
| 9,009,867 B2 * | 4/2015 | Bowen | A41D 1/00 |
| | | | 2/144 |
| 2002/0124294 A1 | 9/2002 | McKenzie et al. | |
| 2008/0067202 A1 | 3/2008 | Silva et al. | |
| 2010/0308086 A1 | 12/2010 | Chapuis | |
| 2012/0045084 A1 | 2/2012 | Groset et al. | |
| 2014/0053854 A1 | 2/2014 | Barry, Jr. | |
| 2014/0304885 A1 | 10/2014 | Oliver | |
| 2015/0196061 A1 | 7/2015 | Oliver | |

\* cited by examiner

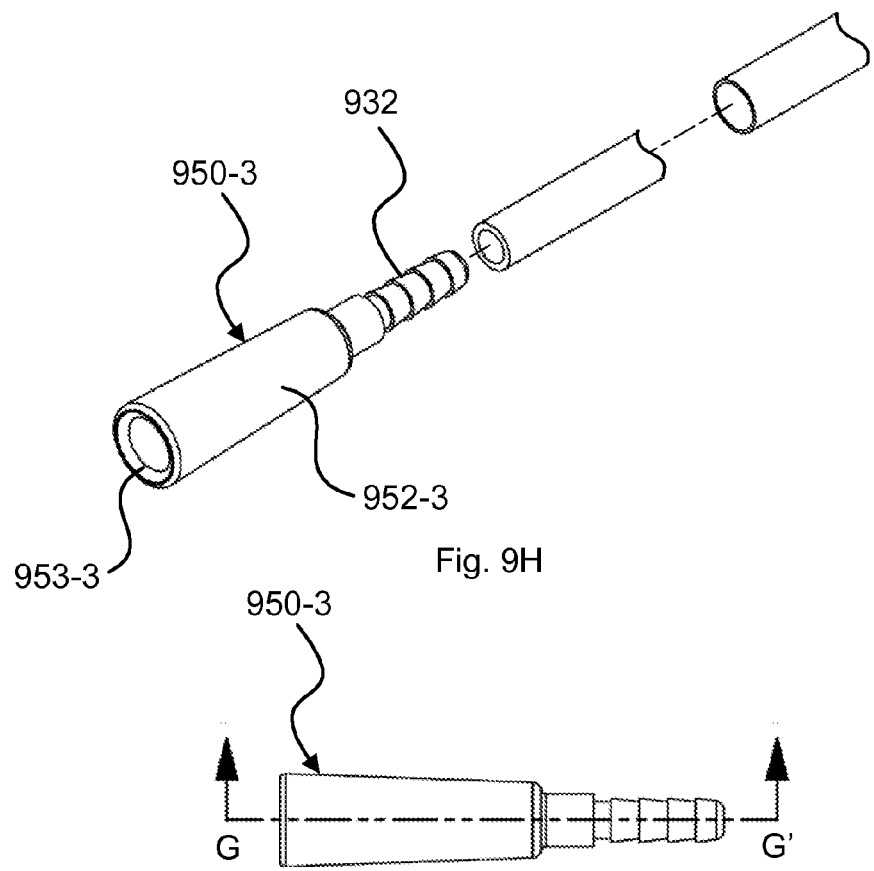
Fig. 9H
Fig. 9I
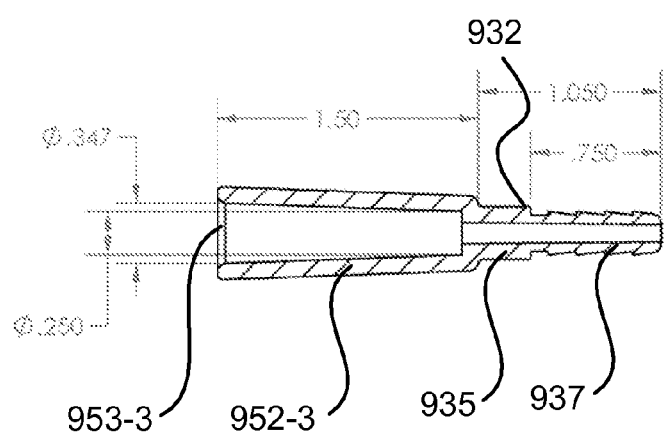
Fig. 9J

CLOTHING TOP FOR TECHNOLOGY CONCEALMENT

CROSS-REFERENCES TO RELATED APPLICATIONS

This application claims benefit of and priority to U.S. Provisional Application No. 62/025,829, filed Jul. 17, 2014, which is incorporated herein by reference for all purposes.

BACKGROUND

This disclosure relates in general to clothing and accessories that are designed to contain a hidden or partially-hidden device and, but not by way of limitation, to assist in consuming of liquids.

Clothing has not evolved as quickly as other personal items have. There is huge inertia holding back innovation in favor of fashion. Technology such as drinking flasks, hydration bladders, vapor pens, oxygen generators, music players, etc. have become necessities of modern life to some. Solutions are needed that would evolve clothing design.

Persons who choose to drink or smoke cigarettes in public must currently do so in a manner that is very conspicuous and even irritating to others. Often, persons who prefer to enjoy their vices in public may wish to be more discreet about their "habit." Clothing is known to carry and conceal items, but not in a manner convenient to users who use the technology.

Users of technology items have strong preferences toward their particular device of choice. Technology items come in different configurations and sizes, for example, there are many different sizes of flasks. Integrating technology into a piece of clothing poses problems.

SUMMARY

Various embodiment of a body-top garment for removably housing a tube assembly is disclosed. The tube assembly has a first end that connects to a mouthpiece, and a second end connects to various types of devices and/or technology. The body-top garment has an elongated pouch with a zipper opening for easy access to the tube assembly. The elongated pouch has a first opening and a second opening to pass at least part of the tube assembly outside the body-top garment. Optionally, the body-top garment also includes one or more pockets with a horizontal opening to hold the various type of devices.

In an embodiment, a body-top garment that removably houses various technology includes an above-the-shoulder element, a garment body below the shoulder line and a tube. The above-the-shoulder element includes a head opening, an elongated pouch, a zipper, a left opening, and a right opening. The head opening extends around at least part of a neck and/or head of a wearer. The elongated pouch traversing around at least a portion of the head opening. The elongated pouch having a left end, a right end, and an opening where the zipper that selectively closes the opening. The left opening of the left end of the elongated pouch has a first reinforcement around the left opening, and a first dimension across the left opening. The right opening of the right end of the elongated pouch has a second reinforcement around the right opening, and a second dimension across the right opening. The garment body below the shoulder line includes a pocket accessible to the wearer that includes a pouch and a horizontal opening. The tube is sized to traverse the elongated pouch and pass through the right opening and left opening. The tube is configured to pass material from outside the right opening to outside the left opening. The horizontal opening is positioned to meet at least part of the tube, and sized to pass the at least part of the tube into the pouch.

In another embodiment, a body-top garment for removably housing various technology that includes an above-the-shoulder element and a tube. The above-the-shoulder element includes an elongated pouch, a left opening and a right opening. The elongated pouch having a left end and a right end. The left opening of the left end of the elongated pouch has a first reinforcement around the left opening and has a first dimension across the left opening of at least one centimeter. The right opening of the right end of the elongated pouch has a second reinforcement around the right opening and a second dimension across the right opening. The tube is sized to traverse the elongated pouch and pass through the right opening and left opening and configured to pass material from outside the right opening to outside the left opening.

In yet another embodiment, a body-top garment that removably houses various technology includes an above-the-shoulder element and a tube. The above-the-shoulder element, comprises an elongated pouch, a left opening and a right opening. The elongated pouch has a left end and a right end. The left opening of the left end of the elongated pouch has a first reinforcement around the left opening and has a first dimension across the left opening of at least one centimeter. The right opening of the right end of the elongated pouch has a second reinforcement around the right opening and the right opening has a second dimension across the right opening. The tube is sized to traverse the elongated pouch and pass through the right opening and left opening and configured to pass material from outside the right opening to outside the left opening.

In one embodiment, a body-top garment that removably houses various technology includes a left opening, a right opening, a tube, and a pocket. The left opening has a first reinforcement around the left opening and a first dimension across the left opening. The right opening has a second reinforcement around the right opening and a second dimension across the right opening. The tube is sized to pass through the left opening and right opening and configured to pass material from outside the right opening to outside the left opening. The pocket is accessible to the wearer and includes a pouch and a horizontal opening. The horizontal opening is positioned to meet at least part of the tube, and sized to pass the at least part of the tube into the pouch.

In still another embodiment, a body-worn device is configured for delivery of vapor or liquid when integrated into a garment. The body-worn device includes a liquid encapsulating device, a tube assembly and a mouthpiece. The liquid encapsulating device passes material out an opening, wherein the liquid is depleted as material passes. The tube assembly includes a first opening, a second opening coupled to the liquid encapsulating device, a cylindrical core that is sealed to not pass the material and flexible to bend, and a woven sheath outside the cylindrical core. The woven sheath is seamless. The cylindrical core is configured to pass material from the second opening to the first opening. The mouthpiece coupled to a first end of the tube.

In still another embodiment, a tube assembly is configured for delivery of vapor or liquid. The tube assembly includes a first tube, a first adaptor, and a second adaptor. The first tube is flexible. The first tube includes a first opening at a first end of the first tube and a second opening at a second end of the first tube. The first tube further includes a cylindrical core for delivering the vapor or liquid between the first and second openings. The first adaptor includes a first tube fitting and a first receptacle connected to the first tube fitting. The first tube fitting is removably connected to the first end of the first tube. The second adaptor includes a second tube fitting and a second receptacle connected to the second tube fitting. The second tube fitting is removably connected to the second end of the first tube. The first adaptor, the first tube and the second adaptor are configured for removably connecting a liquid encapsulating device to a mouthpiece. At least one of the first adaptor or the second adaptor controls a flow of the vapor or liquid between the liquid encapsulating device and the mouthpiece.

Further areas of applicability of the present disclosure will become apparent from the detailed description provided hereinafter. It should be understood that the detailed description and specific examples, while indicating various embodiments, are intended for purposes of illustration only and are not intended to necessarily limit the scope of the disclosure.

BRIEF DESCRIPTION OF THE DRAWINGS

The present disclosure is described in conjunction with the appended figures:

FIG. 9H illustrates a perspective view of one embodiment of the adaptor and an end portion of the tube assembly where various parts are shown in an exploded view;

FIG. 9I illustrates a plan view of the adaptor of FIG. 9H;

FIG. 9J illustrates a cross-sectional view of the adaptor of FIGS. 9H and 9I, viewed along line G-G' of FIG. 9I;

In the appended figures, similar components and/or features may have the same reference label. Further, various components of the same type may be distinguished by following the reference label by a dash and a second label that distinguishes among the similar components. If only the first reference label is used in the specification, the description is applicable to any one of the similar components having the same first reference label irrespective of the second reference label.

DETAILED DESCRIPTION OF THE EXEMPLARY EMBODIMENTS

The ensuing description provides preferred exemplary embodiment(s) only, and is not intended to limit the scope, applicability or configuration of the disclosure. Rather, the ensuing description of the preferred exemplary embodiment(s) will provide those skilled in the art with an enabling description for implementing a preferred exemplary embodiment. It is understood that various changes may be made in the function and arrangement of elements without departing from the spirit and scope as set forth in the appended claims.

Figure 1A:
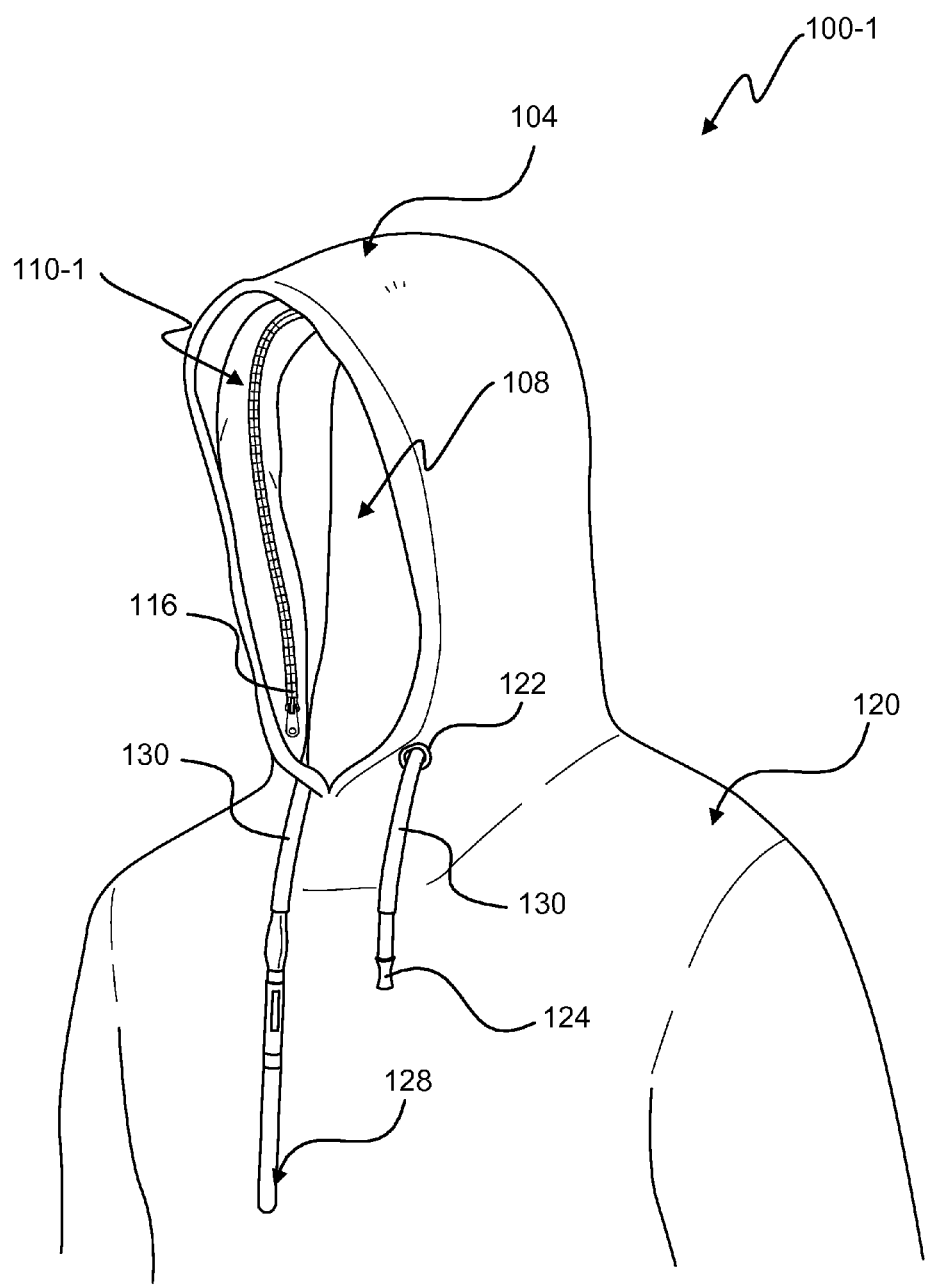
FIGS. 1A-1D illustrate perspective views of various embodiments of a body-top garment for housing a liquid encapsulating device.

Referring first to FIG. 1A, an embodiment of a clothing top, body-top garment or sweatshirt 100-1 for accommodating technology is shown. This embodiment is long-sleeved with an exposed zipper 116 away from the leading edge of the head opening 108. The sweatshirt 100-1 includes an above-the-shoulder element or hood 104 that is attached to a garment body 120. In another embodiment, the hood 104 may be removable from the garment body 120. A head opening 108 accommodates the face of the wearer so that the other sides of the wearer's head is kept covered when the hood 104 is deployed. The hood 104 can be pulled back off the wearer's head to bunch-up around the back of the neck of the wearer. Various fabrics may be used for the sweatshirt 100-1 and there may be different seams and stitching used in the assembly.

This embodiment of the sweatshirt 100-1 accommodates embedding technology into the clothing in a way that allows easy removal. An elongated pouch 110-1 has an opening defined and/or reinforced by a grommet 122 on each end to allow threading of technology into the hood 104 around the head opening 108. The grommets 122 are located on the exterior of the hood 108 on either side of the wearer's neck in this embodiment. The size of the elongated pouch 110-1 is defined by its path between the location of the two grommets 122 and the thickness of the technology embedded. In this embodiment, the elongated pouch 110-1 is about 18 inches long, but is at least 10, 12, 14, 16, 20, 22, 24, or 26 inches in other embodiments; and about 2 inches wide, but is less than 4, 3, 1.5, 1, or 0.75 inches in other embodiments.

It can be difficult to remove the technology, but this embodiment includes an exposed zipper 116. Although this embodiment has an exposed zipper 116, other embodiments may cover the zipper to be completely or substantially hidden from view when worn by a wearer. As shown, the exposed zipper 116 closes off the elongated pouch 110-1, which is the normal operational configuration. To remove the technology for cleaning of the sweatshirt 100-1, the exposed zipper 116 is opened to easily access the technology. Although the zipper is exposed and away from the leading edge of the head opening, in other embodiments the zipper could be covered with a flap of clothing material and/or be placed elsewhere in the hood 104. For example, the elongated pouch could be around the back of the neck of the wearer or even below the shoulders in the garment body 120. The embedded zipper traverses about 90% of the elongated pouch 110-1 in this embodiment, but could be at least 100%, 95%, 85%, 80%, 75%, 70%, or 65% in other embodiments. In an alternative embodiment, there could be multiple zippers that traverse a subsection of the elongated pouch 110-1 to allow access to the technology.

Various technology can be embedded into the sweatshirt 100-1 at the option of the wearer. Shown is a vaporizing device 128 that takes encapsulated liquids, wax, oils, and/or dry material ("consumable material") for heating until vapor is emitted without producing smoke. In some embodiments, both vapor and smoke are emitted. A chamber in the vaporizing device 128 allows the wearer to add the consumable material after the vapor is rendered from it. A tube assembly 130 has the vaporizing device 128 on one end and a mouthpiece 124 on the other. The tube assembly 130 is thread through the grommets 122 and the elongated pouch 110-1 to optionally serve as a drawstring for the head opening 108. The mouthpiece 124 extends from the grommet 122 to the wearers mouth such that the tube assembly 130 delivers the vapor from the vaporizing device 128. The grommet 122 is within 5 inches from the mouth of the wearer during normal operation, but could be less than 3, 4, 6, 8, 10, or 12 inches in other embodiments.

Figure 1B:
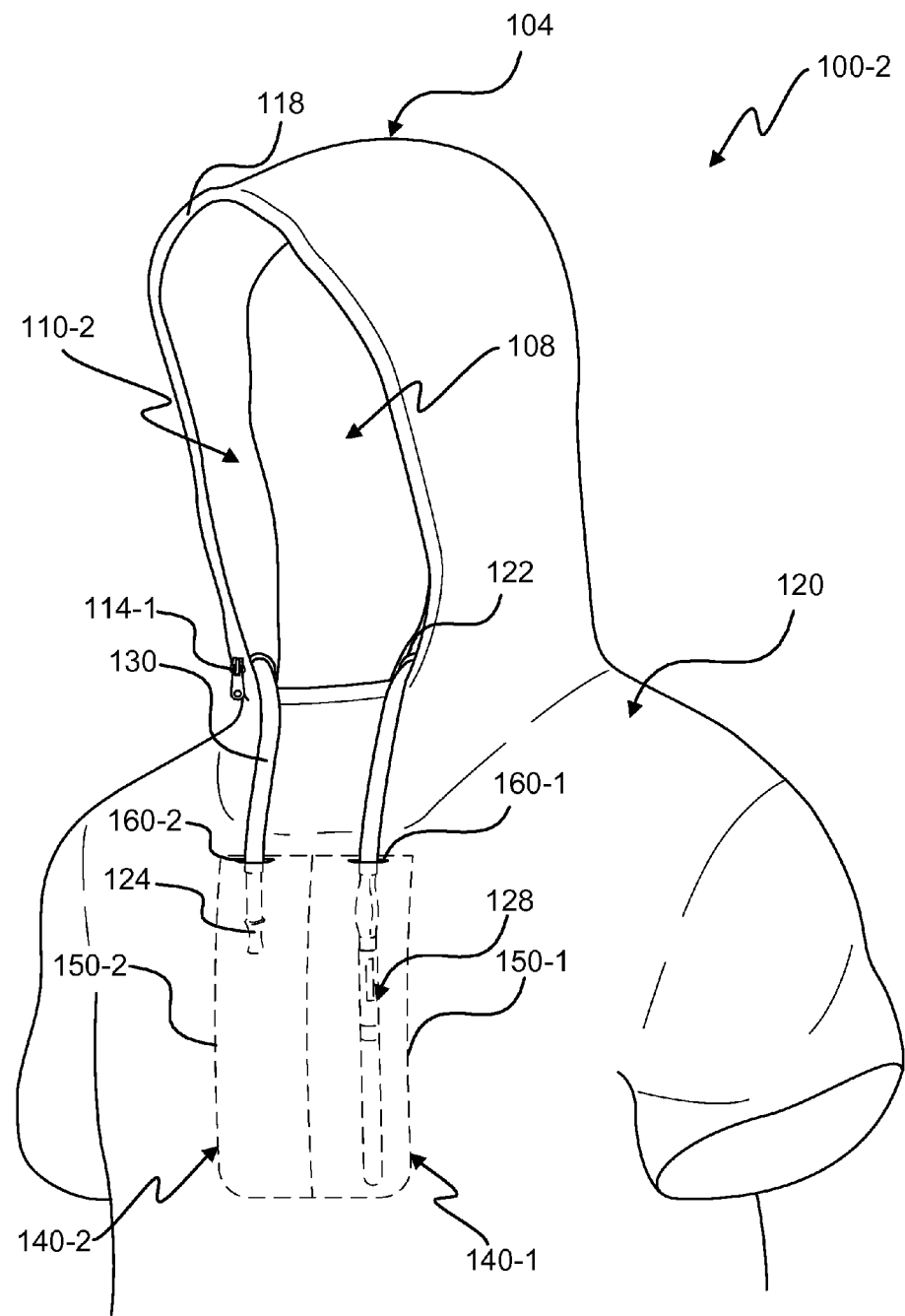

Referring next to FIG. 1B, one view of an alternative embodiment of a sweatshirt 100-2 for housing the vaporizing device 128 is shown. In this example, the sweatshirt 100-2 is short-sleeved with pockets 140 and has an embedded zipper 114-1 at the leading edge of the head opening 108. Flaps 118 at least partially cover the embedded zipper 114-1 along some or all of the embedded zipper's 114-1 length. The elongated pouch 110-2 also meets the leading edge of the head opening 108 as the embedded zipper 114-1 defines one edge of the elongated pouch 110-2 in this embodiment. In other embodiments, the embedded zipper could give access to the beginning and ends of the elongated pouch with a portion in the middle of the elongated pouch not being opened with the embedded zipper. The embedded zipper 114-1 could have a metal or plastic track with the zipper pull being either metal or plastic. The openings of the elongated pouch 110-2 (i.e., grommets 122) are positioned to face the interior of the hood 104 in this embodiment. The grommets 122 are separated from each other at a distance of 3 inches, but a separation of no less than 0.75, 1, 1.5, 2, 3, 5, 6, or 7 inches could be used in various embodiments.

This embodiment has pockets 140 that are positioned on the front of the sweatshirt 100-2 to hold whatever technology is on the ends of the tube assembly 130. Here, we have a mouthpiece 124 and a vaporizing device 128, but other embodiments could have other technology, for example ear buds and music player, flask or liquid bladder, oxygen generator, asthma inhaler, other nasal/mouth inhaler, over-the-face/oral/nasal mask, etc. The pockets 140 are positioned between and slightly lower than the armholes of the sweatshirt 100-2 in this embodiment, but could be positioned higher or lower in other embodiments for easy access by the wearer. The bottom of the pockets 140 could partially support the weight of the various technology attached to the tube assembly 130.

The pockets 140 include: a left front pocket 140-1 defined by a left pouch 150-1 with a left horizontal opening 160-1, and a right front pocket 140-2 defined by a right pouch 150-2 with a right horizontal opening 160-2. The right front pouch 150-2 is immediately adjacent to the left pouch 150-1 in this embodiment, but other embodiments could separate the right pouch 150-2 from the left pouch 150-1 by at least 1, 2, 4, 6, 8, 10, 12, or 14 inches. In some embodiments, the pocket 140 could be one integral pocket without any compartmentalizing and have either one or two horizontal openings 160.

The left and right pouches 150-1, 150-2 receive the mouthpiece 124 and the vaporizing device 128, respectively, or vice versa, depending on the wearer's preference. The left and right pouches 150-1, 150-2 each have a depth to fully contain the technology and an end portion of the tube assembly 130. This way, the technology is concealed in the pockets 140 and the sweatshirt 100-2 looks like a regular sweatshirt with a drawstring. The left and right pouches 150-1, 150-2 are positioned inside the garment body 102 and are substantially not visible from the exterior.

The pouches 150 could be made of various lining materials, such as fabric, woven, or nonwoven materials. In some embodiments, the pouches 150 could be made of plastic or treated fabric to be waterproof and/or heat resistant. In some embodiments, the pouches 150 are permanently joined to the hood 104 by sewing, adhering, or any other suitable attaching mechanisms. In some embodiments, the pouches 150 are removably joined to the hood 104 using hook-and-loop fasteners, snap buttons, zippers, sliding/ziplock fasteners, and any other suitable mechanisms.

The left and right horizontal opening 160-1, 160-2 are sized to pass through various technologies into the pockets 140-1, 140-2. In some embodiments, the horizontal openings 160-1, 160-2 are stretchable openings that could be stretched to pass through technology of various sizes. The horizontal openings 160 are reinforced by buttonhole stitches in this embodiment, but could be reinforced by grommets with suitable shapes and sizes.

Figure 1C:
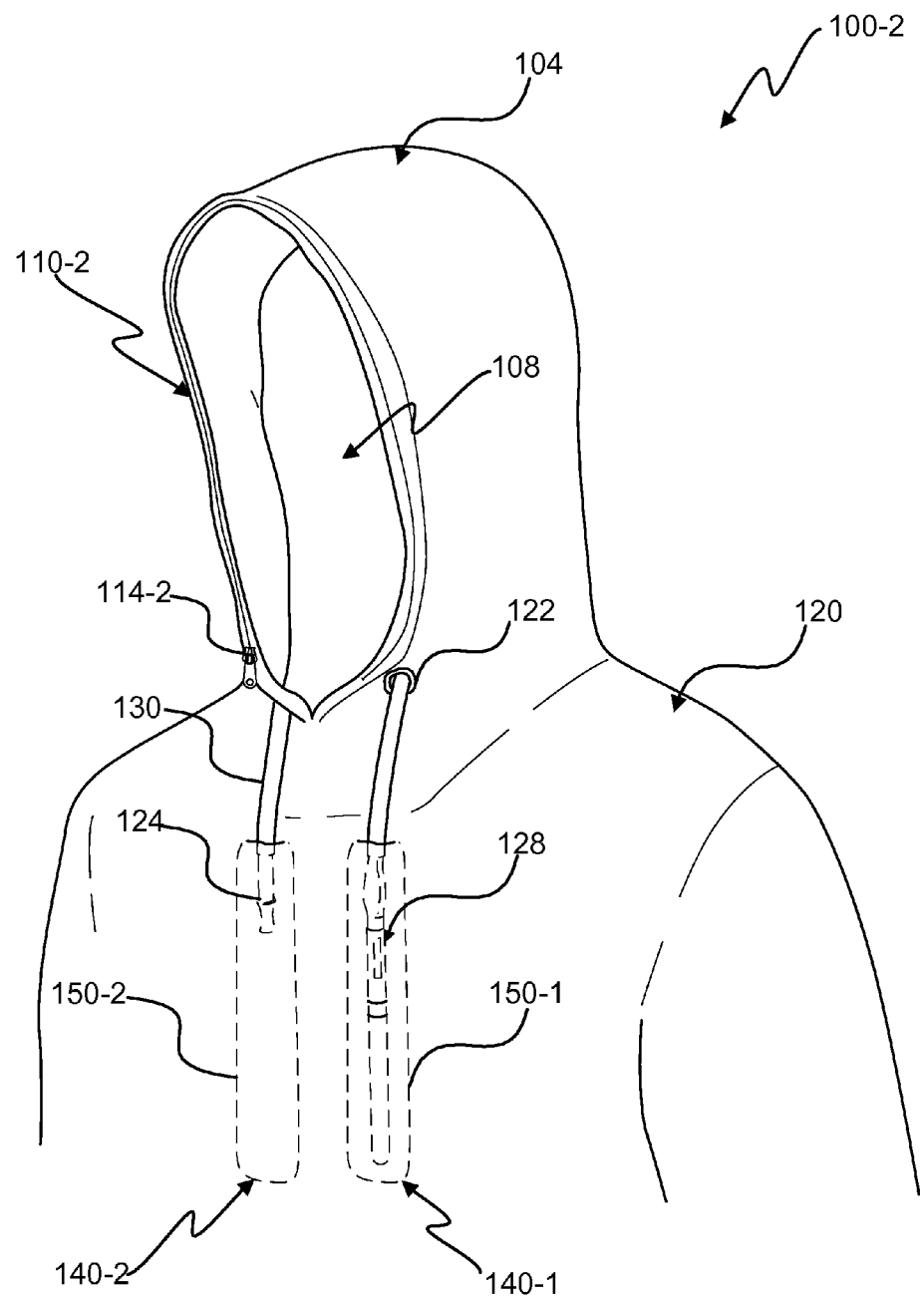

With reference to FIG. 1C, one view of an embodiment of a sweatshirt 100-3 for housing the vaporizing device 128 is shown. In this example, the embedded zipper 114-2 for opening and closing the elongated pouch 110-2 is not visible. The left and right pouches 150-1, 150-2 are horizontally separated from each other by at least 1.5 inches. The reduced width dimension of the left and right pouches 150-1, 150-2 limits lateral movements of the vaporizing device 128 and the mouthpiece 124.

The left and right pouch 150-1 and the left horizontal opening 160-1 are substantially aligned with the grommet 122 above the left horizontal opening 160-1. The right pouch 150-2 and the right horizontal opening 160-2 are substantially aligned with the other grommet 122 above the right horizontal opening 160-2. This way, the end portions of the tube assembly 130, the mouthpiece 124, and the vaporizing device 128 fall from the grommets 122 into the pouches 150-1, 150-2 along the natural extension of the tube assembly 130.

Figure 1D:
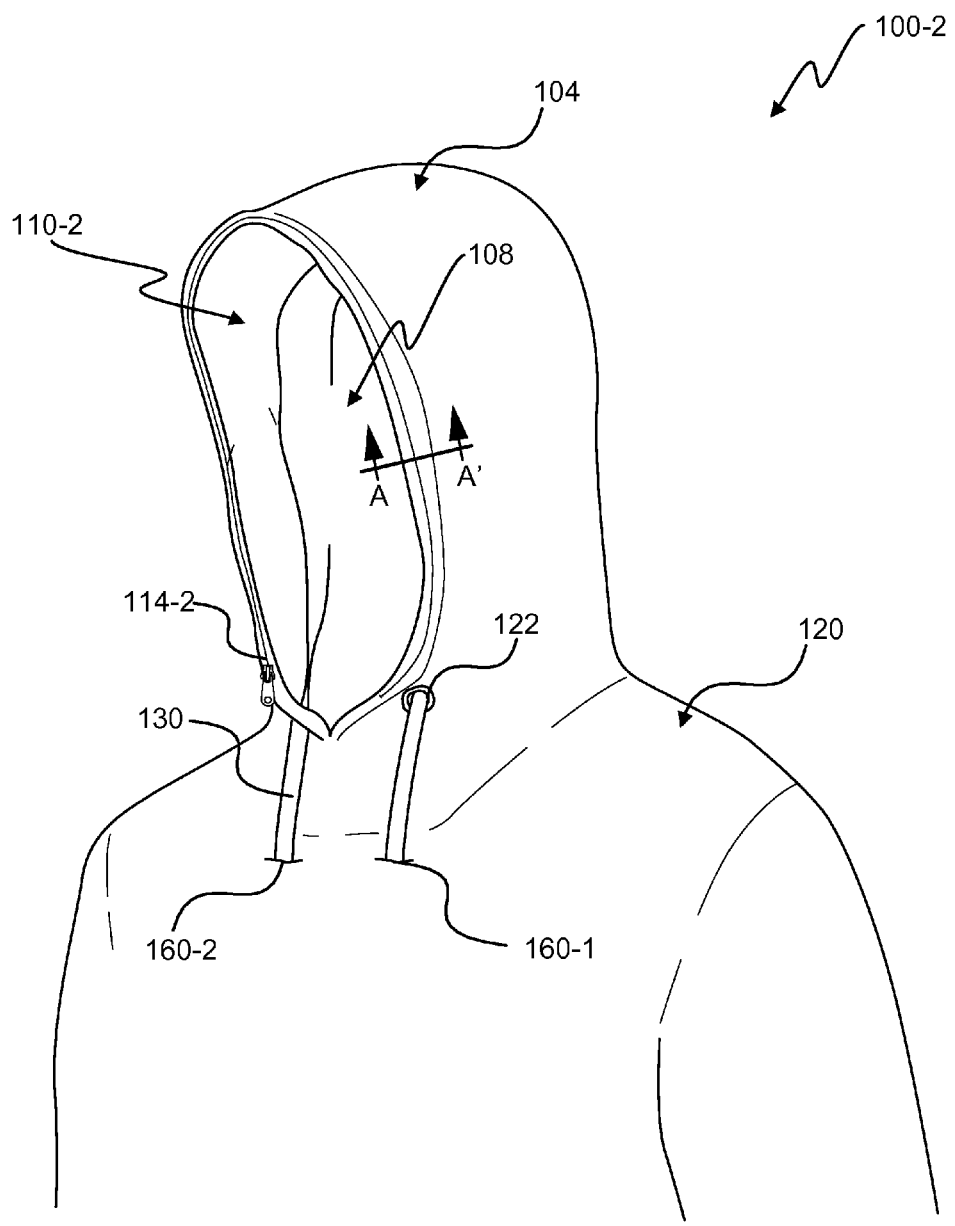

With reference to FIG. 1D, another view of an alternative embodiment of a sweatshirt 100-3 for housing the vaporizing device 128 is shown. This embodiment is the same as the embodiment of FIG. 1C, but does not show the contour of the left and right pouches 150 and the concealed vaporizing device 128.

Figure 2:
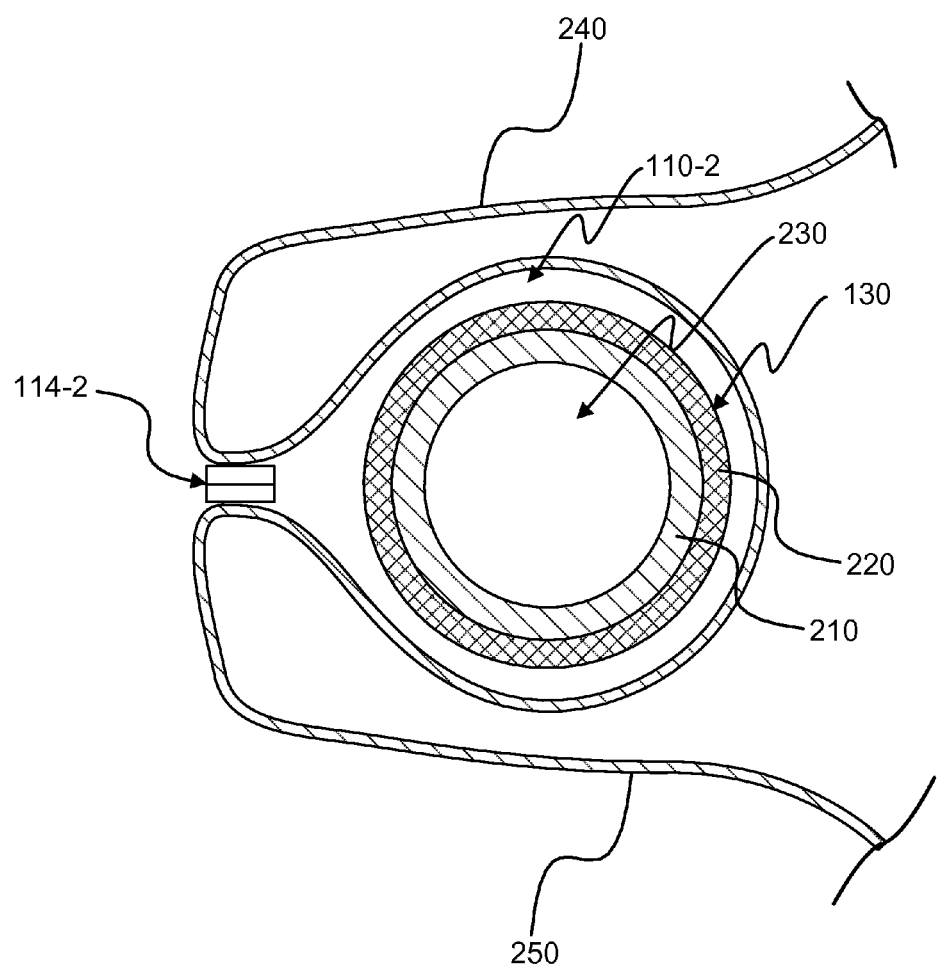
FIG. 2 illustrates a cross-sectional view of an embodiment of an elongated pouch of the body-top garment of FIG. 1D, viewed along line A-A' of FIG. 1D.

With reference to FIG. 2, a cross-sectional view of the leading edge portion of the hood 104, viewed along line A-A' of FIG. 1D, is shown. The hood 104 has an outer layer 240 exposed to the elements and an inner layer 250 facing the wearer. The outer layer 240 and the inner layer 250 meet at the leading edge of the head opening 108 and are joined by the embedded zipper 114-2 that selectively closes the elongated pouch 100-2. The elongated pouch 110-2 is sandwiched between the outer layer 240 and the inner layer 250. The tube assembly 130 is received in the elongated pouch 110-2.

In this embodiment, the outer layer 240, the inner layer 250 and the elongated pouch 110-2 are formed by one integral piece of woven material. In other embodiments, the outer layer 240, the inner layer 250, and the elongated pouch 110-2 may be formed by individual pieces of materials joined together by the embedded zipper 114-2 and/or other stitching. The outer layer 240, the inner layer 250, and the pouch 110-2 may be made of the same or different materials, such as fabric, leather, plastic, natural or synthetic materials, woven or non-woven materials, and/or any other materials suitable for clothing. The outer layer 240 and/or the inner layer 250 may be treated to protect the wearer from various weather elements and/or treated for fire proofing.

The zipper tape of the embedded zipper 114-2 is joined to the interior surface of the elongated pouch 110-2 by sewing, adhering, stapling, or any suitable attaching mechanism. When the embedded zipper 114-2 is closed, the outer layer 240 and the inner layer 250 of the hood 104 touch or almost touch each other, and the zipper teeth of the embedded zipper 114-2 are substantially or completely covered and invisible from the outside. In some embodiments, the zipper tape of the embedded zipper 114-2 is joined to the exterior surfaces of the outer layer 240 and the inner layer 250 and is covered by a flap.

Although zippers are described as one mechanism to open and close the elongated pouch 110, the elongated pouch 110 can be opened and closed using hook-and-loop fasteners, sliding/ziplock fasteners, buttons, snap buttons, tie strings, drawstrings, and/or any other suitable closing mechanisms. In some embodiments, the elongated pouch 110 does not include such closing mechanism. The elongated pouch 110 has a longitudinal access defined by overlapping edge portions of the fabric forming the elongated pouch 110.

The tube assembly 130 includes a cylindrical core or tube inner layer 210 and a woven sheath or tube outer layer 220. In some embodiments, the tube assembly 130 includes more than two tube layers. In other embodiments, the tube assembly 130 includes only one tube layer. The tube inner layer 210 defines conduit 230 for delivering various materials, such as vapor, liquids, gel, solid, or any fluid that can flow from one end of the tube assembly 130 to the other end of the tube assembly 130. In some embodiments, the diameter of the conduit 230 (or the inner diameter of the tube inner layer 210) is no less than 0.1, 0.2, 0.4, 0.6, or 0.8 inch. The outer diameter of the tube inner layer 210 is no less than 0.1, 0.2, 0.4, 0.6, or 0.8 inch. In one embodiment, the inner diameter of the tuber inner layer 210 is 0.25 inch (or 6.4 mm) and the outer diameter of the tuber inner layer 210 is 0.3 inch (or 7.6 mm).

The tube inner layer 210 is made of plastic materials, such as silicone, PVC, EVA, TPU, HDPE, LDPE, PP, or any suitable materials approved by the food and drug administration. The working temperature for the tube inner layer 210 is from $-5°$ C. to $65°$ C. In some embodiments, the tube inner layer 210 can be formed with particular materials or treated so that the working temperature of the tube inner layer 210 is lower than $-5°$ C. and/or higher than $65°$ C. In some embodiments, the tube outer layer 220 is made of materials used in the manufacture of drawstrings for clothing so as to resemble the look of a drawstring of a sweatshirt. In other embodiments, the tube outer layer 220 is made of materials, such as fabric, plastic, foam, aluminum, and so on, to maintain the temperature of the tube inner layer 210 or to achieve other desired properties.

Figure 3A:
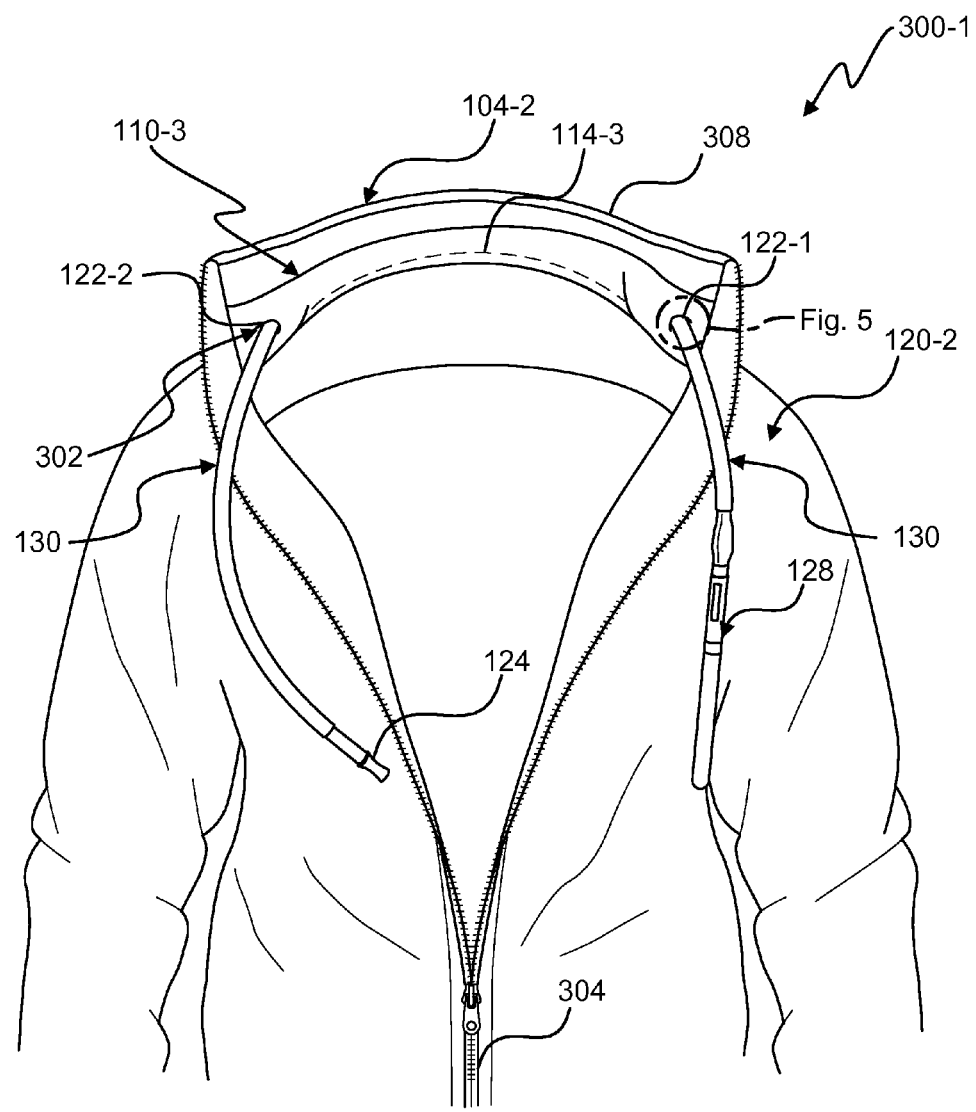
FIGS. 3A-3E illustrate views of various embodiments of another body-top garment for housing the liquid encapsulating device.

Referring next to FIG. 3A, another embodiment of a clothing top, body-top garment, or jacket 300-1 for accommodating various technologies is shown. The jacket 300-1 includes an above-the-shoulder element or collar 104-2 that is attached to a garment body 120-2. The jacket 300-1 is long-sleeved and has a front zipper 304 that runs from the top to the bottom of the jacket 300-1. The front zipper 304 divides the front of the jacket 300-1 into a left half 306-1 and a right half 306-2. When the front zipper 304 is closed, the collar 104-2 defines a neck opening to accommodate the wearer's neck. The jacket 300-1 further includes an elongated pouch 110-3 located at the interior of the collar 104-2. The elongated pouch 110-3 accommodates various technologies. In this embodiment, the tube assembly 130 is similar to that described with reference to FIGS. 1A-2 above.

The elongated pouch 110-3 is positioned away from and extends parallel to the top edge 308 of the collar 104-2. In this embodiment, the elongated pouch 110-3 extends along the entire collar 104-2, but extends at least 50%, 60%, 70%, 80%, or 90% of the collar 104-2 in other embodiments. The elongated pouch 110-3 has an opening 302 defined and reinforced by a grommet 122 on each end to allow threading of the tube assembly 130 into the elongated pouch 110-3 around the neck opening. The elongated pouch 110-3 further includes a zipper 114-3 along the extension of the elongated pouch 110-3 that allows for easy removal of the tube assembly 130. The zipper 114-3 is positioned to face the interior surface of the collar 104-2 so as not to touch and/or rub against the wearer's neck.

The elongated pouch 110-3 is joined to the interior of the collar 104-2 at either end of the elongated pouch 110-3. In some embodiments, the elongated pouch 110-3 is further joined to the collar 104-2 along its longitudinal dimension. In some embodiments, the elongated pouch 110-3 is permanently joined to the collar 104-2 by stitching, adhering, gluing, stapling, and so on. In some embodiments, the elongated pouch 110-3 is removably joined to the collar 104-2 using snap buttons, hook-and-loop fasteners, zippers, sliding/ziplock fasteners, and so on.

Figure 3B:
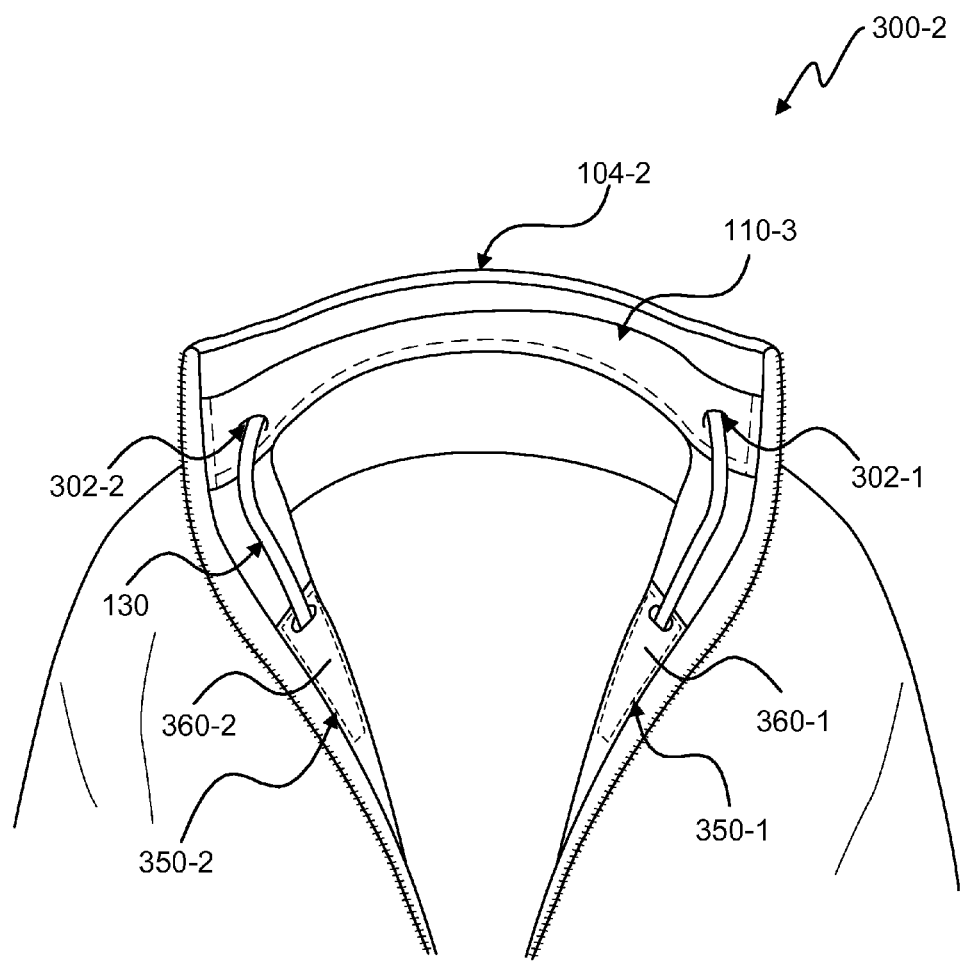

Referring next to FIG. 3B, another embodiment of a clothing top, body-top garment, or jacket 300-2 for accommodating various technologies is shown. In this embodiment, the jacket 300-2 further includes a left inner pocket 350-1 and a right inner pocket 350-2 positioned on the interior of the left half 306-1 and the right half 306-2 of the jacket 300-2, respectively.

The left inner pocket 350-1 is defined by a left inner pouch 360-1 with a left horizontal opening 370-1. The right inner pocket 350-2 is defined by a right inner pouch 360-2 with a right horizontal opening 370-2. The inner pockets 350 of this embodiment function similar to the pockets 140 of FIGS. 1B and 1C. Each of the inner pouches 360 receives an end portion of the tube assembly 130 and component(s) of various technologies attached thereto. Different from the embodiments of FIGS. 1B and 1C, the left and right horizontal openings 370-1, 370-2 of this embodiment face the interior of the jacket 300-2. Therefore, the tube assembly 130 extends from the openings 302 of the elongate pouch 110-3 to the horizontal openings 370 of the inner pockets 350 along the interior surface of the jacket 300-2. When the front zipper 304 is closed, the tube assembly 130 is completely or substantially hidden from view.

Figure 3C:
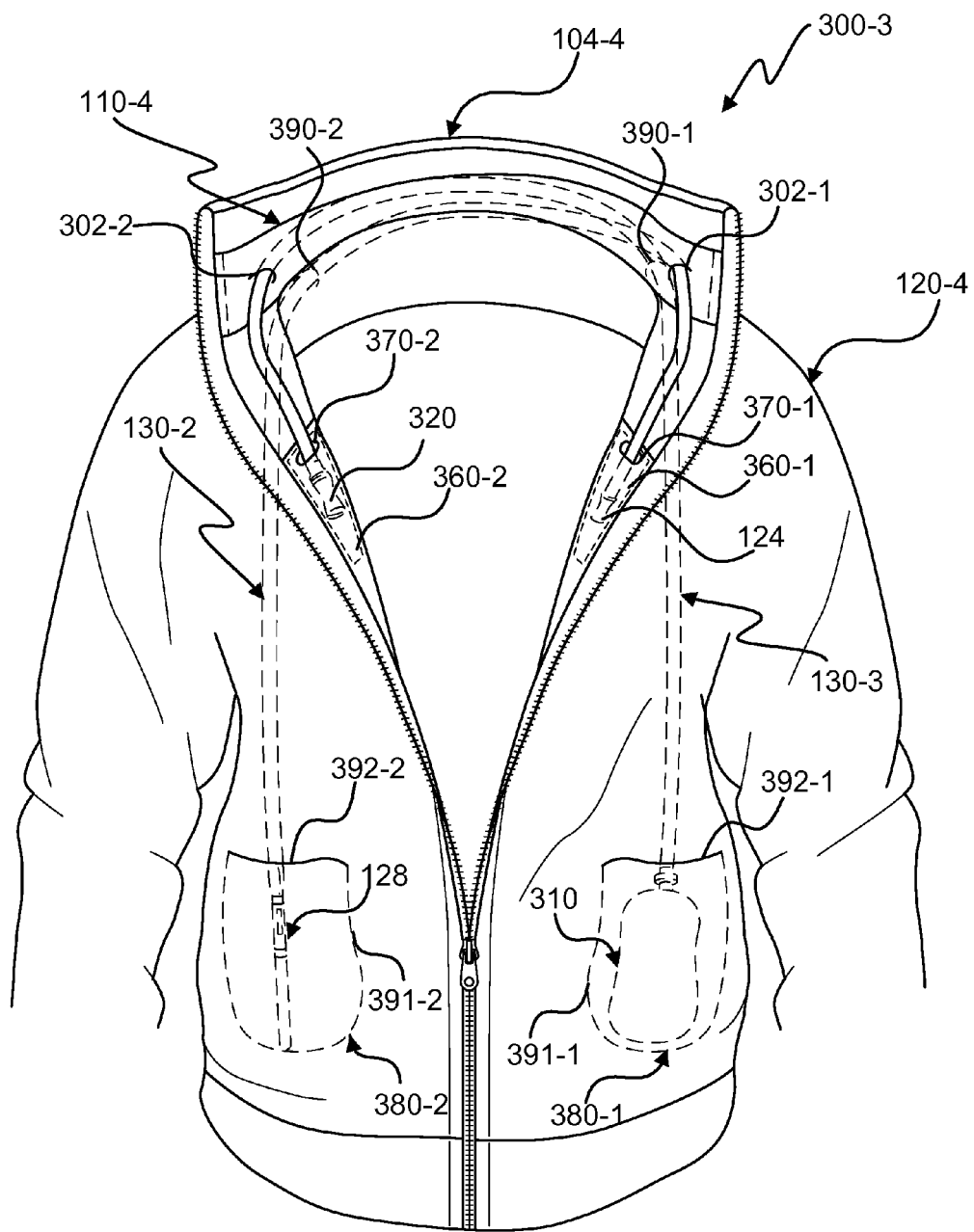

With reference to FIG. 3C, another embodiment of a clothing top, body-top garment, or jacket 300-3 for accommodating multiple technologies is shown. In this embodiment, the jacket 300-3 further includes a left hand pocket 380-1 and a right hand pocket 380-2. Each hand pocket 380 has a hand pouch 391 and a horizontal opening 392 that allows for access from both the inside and outside of the jacket 300-3. In some embodiments, the horizontal openings 392 only allows for access from the inside of the jacket 300-3. The elongated pouch 110-4 includes an additional pair of secondary openings 390 near either end of the elongated pouch 110-4. The elongated pouch 110-4 and the hand pockets 380 cooperate to accommodate two technologies.

The first technology is the vaporizing device 128 similar to that described with reference to FIGS. 1A-1C above. The vaporizing device 128 and the cooperating mouthpiece 124 are attached to either end of a first tube assembly 130-2. The second technology is a drinking apparatus. The drinking apparatus includes a flask or flexible bladder 310 and a cooperating bite valve 320 attached to either end of a second tube assembly 130-3. The first and second tube assemblies 130-2, 130-3 are similar to the tube assembly 130 described above with reference to FIG. 2 but are longer. The jacket 300-3 can accommodate other technologies. The two technologies can be the same technology for a longer supply.

The first technology is housed in the jacket 300-3 in the following manner. The mouthpiece 124 is received in the left inner pouch 360-1 and the vaporizing device 128 is received in the right hand pouch 391-2. The first tube assembly 130-2 is thread out of the left inner pouch 360-1 through the left horizontal opening 370-1, then thread into the elongated pouch 110-4 through the opening 302-1 above the left horizontal opening 370-1, then thread out of the elongated pouch 110-4 through the right secondary opening 390-2, and then thread into the right hand pouch 391-2 through the horizontal opening 392-2.

The second technology is housed in the jacket 300-3 in a similar manner. The bite valve 320 is received in the right inner pouch 360-2 and the bladder 320 is received in the left hand pouch 391-1. The second tube assembly 130-3 is thread out of the right inner pouch 360-2 through the right horizontal opening 370-2, then thread into the elongated pouch 110-4 through the opening 302-2 above the right horizontal opening 370-2, then thread out of the elongated pouch 110-4 through the left secondary opening 390-1, and then thread into the left hand pouch 391-1 through the horizontal opening 392-1.

This embodiment can accommodate technologies of much greater weight without creating much discomfort to the wearer because most of the weight of the housed technologies is supported by the hand pockets 380. The hand pockets 380 help to spread the weight from around the neck of the wearer to the shoulders of the wearer.

Figure 3D:
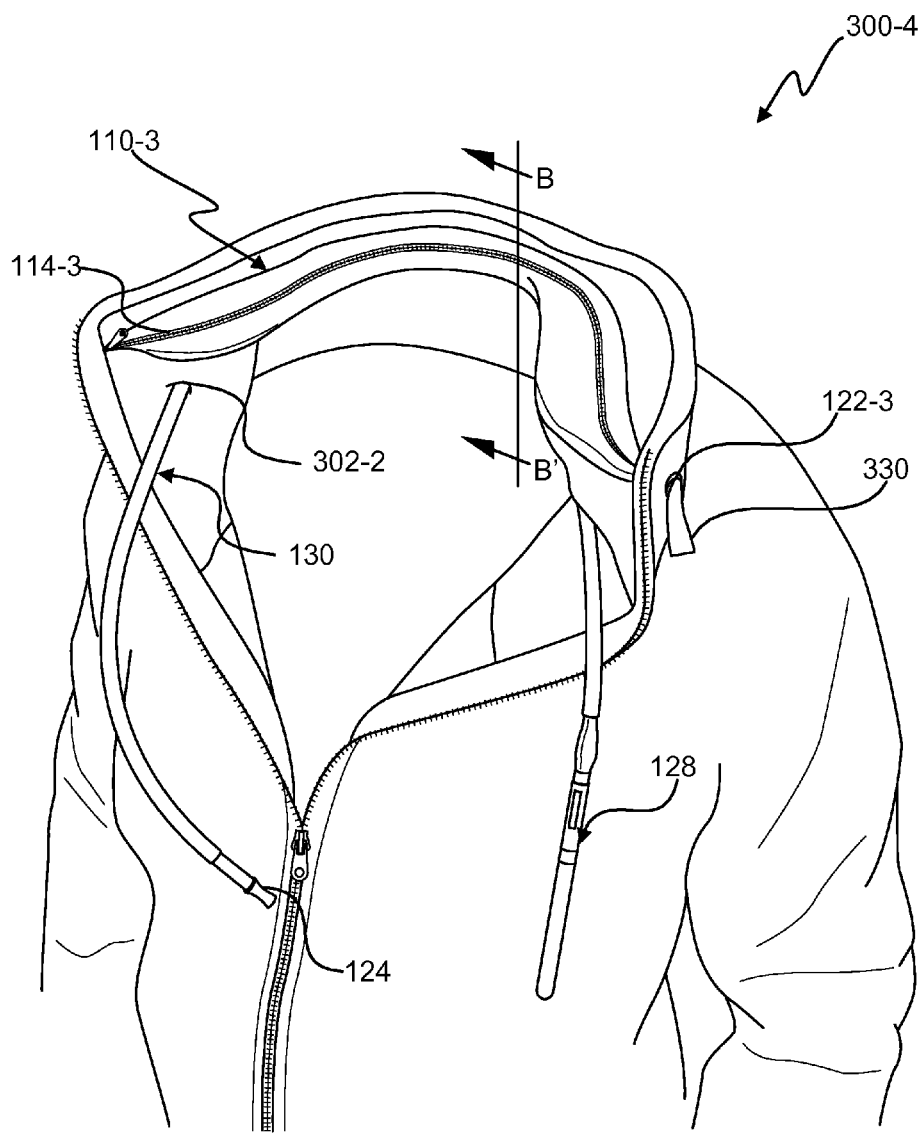
Figure 3E:
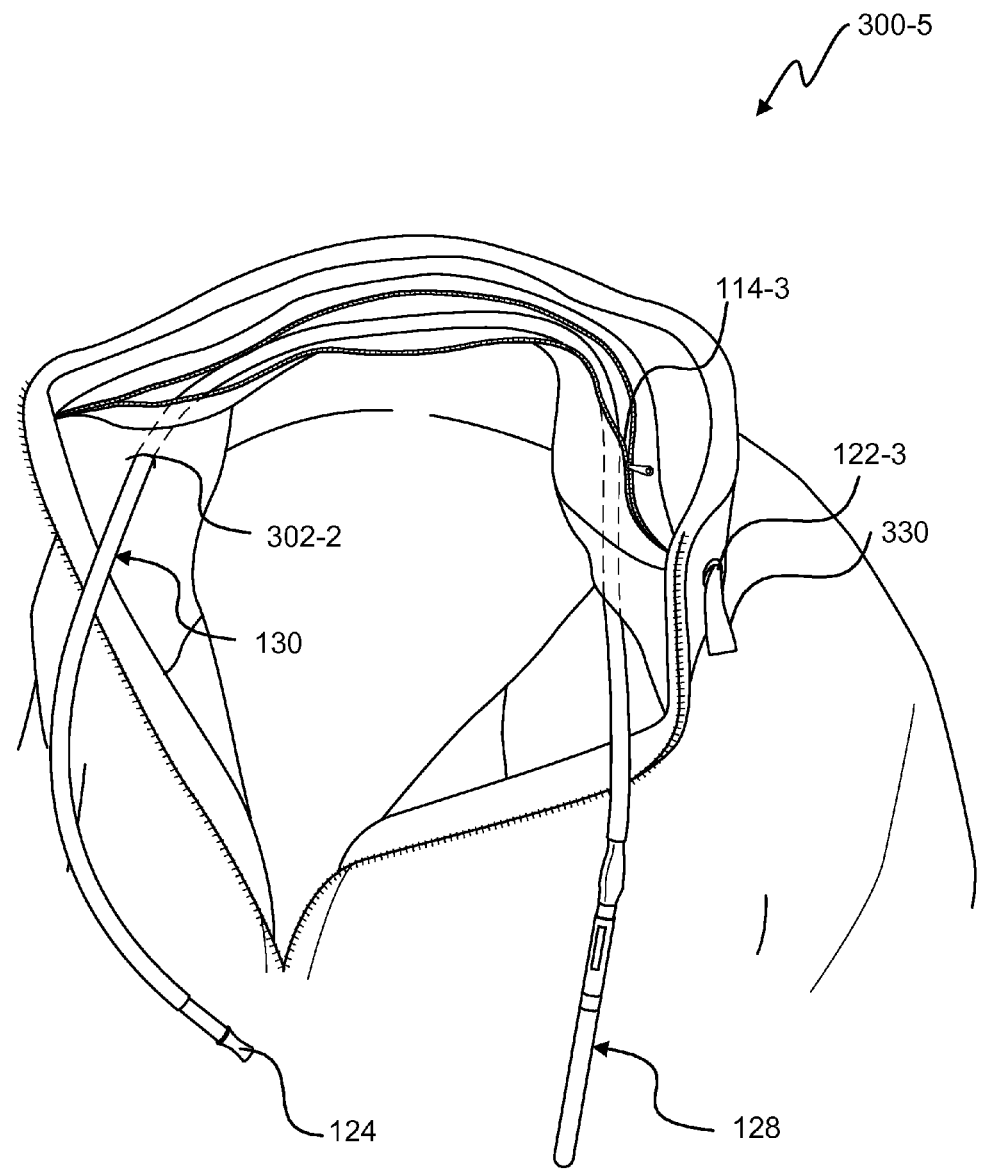

With reference to FIGS. 3D-3E, views of another embodiment of a clothing top, body-top garment, or jacket 300-4 for accommodating various technologies is shown. In FIG. 3D, the embedded zipper 114-3 is closed. In FIG. 3E, the embedded zipper 114-3 is open. This embodiment further includes a compartment defined by the collar 104-2 for receiving a drawstring 330. The compartment 325 has two openings positioned on the exterior of the collar 104-2 for threading the drawstring 330. The openings are located in close proximity to the front zipper 304 and are each reinforced by a grommet 122-3. When the drawstring 330 is pulled, the collar 104-2 can be tightened around the neck of the wearer.

Figure 4:
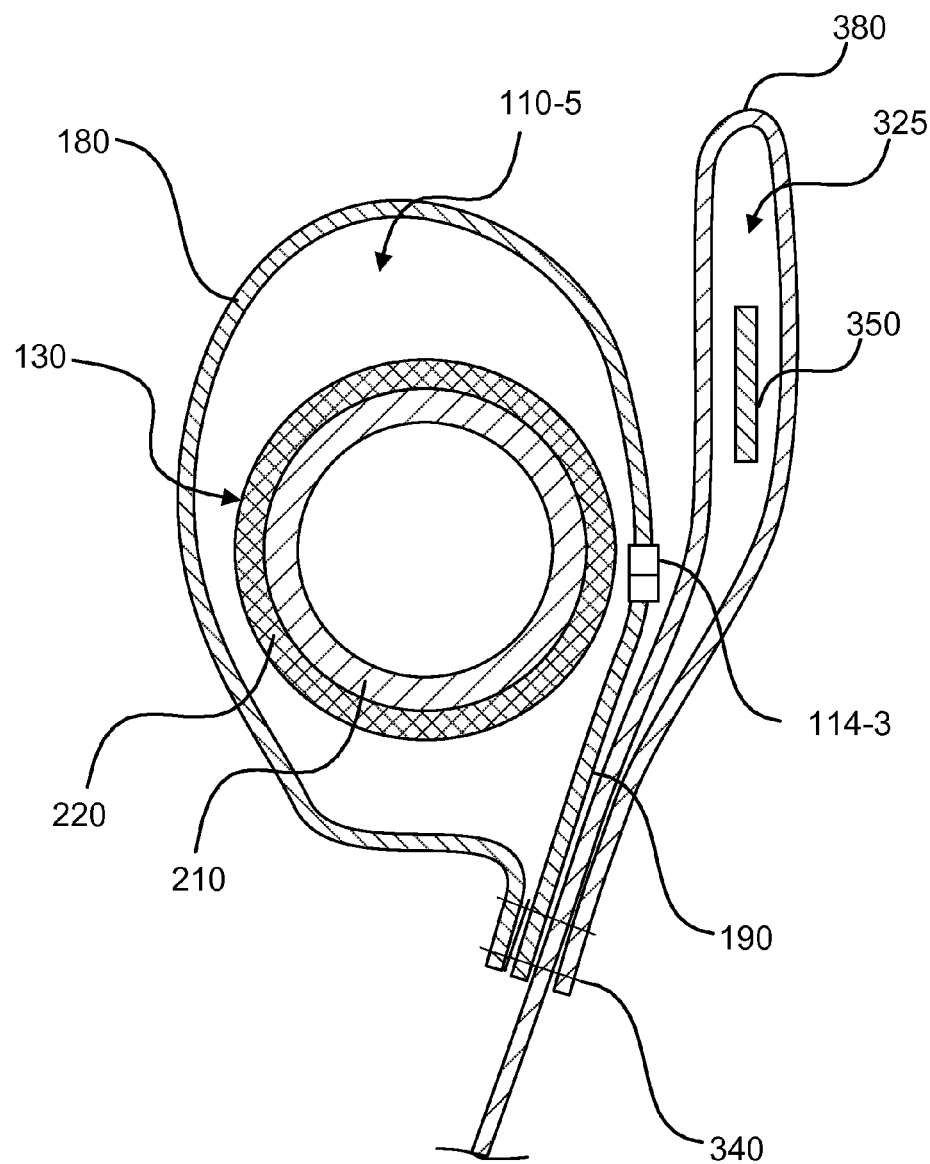
FIG. 4 illustrates a cross-sectional view of an embodiment of the elongated pouch of the body-top garment of FIG. 3D, viewed along line B-B' of FIG. 3D.

With further reference to FIG. 4, a cross-sectional view of the compartment 325 and the elongated pouch 110-5, viewed along line B-B' of FIG. 3D, is shown. The compartment 325 is formed by folding an end portion of the material forming the collar 104-2. In this embodiment, the end portion is folded outwardly, but could be folded inwardly in other embodiments. The folding line defines the top edge 308 of the collar 104-2. The folded end portion is joined to the collar material by a line of stitching 340.

The elongated pouch 110-5 is made of two pieces of materials: a neck-facing piece 180 and a collar-facing piece 190. One longitudinal edge of the neck-facing piece 180 and one longitudinal edge of the collar-facing piece 190 are aligned with each other and are joined to the collar 104-2 by the same line of stitching 340 for creating the compartment 325. The other longitudinal edge of the neck-facing piece 180 and the other longitudinal edge of the collar-facing piece 190 are joined together by the embedded zipper 114-3. The distance between the longitudinal edges of the neck-facing piece 180 defines a width dimension of the neck-facing piece 180. The distance between the longitudinal edges of the collar-facing piece 190 defines a width dimension of the collar-facing piece 190. The width dimension of the neck-facing piece 180 is greater than the width dimension of the collar-facing piece 190. As such, the embedded zipper 114-3 faces the collar 104-2 and does not contact and/or rub against the neck of the wearer. In some embodiments, the width dimension of the neck-facing piece 180 is no less than 1.2, 1.5, 1.8, 2, 3, 4, 5, 6 times the width dimension of the collar-facing piece 190.

Figure 5A:
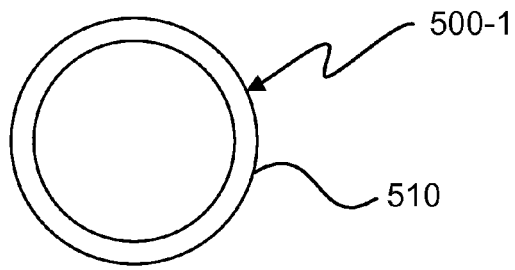
FIGS. 5A-5E illustrates structural diagrams of embodiments of reinforcement around an opening of the elongated pouch of the body-top garment.
Figure 5B:
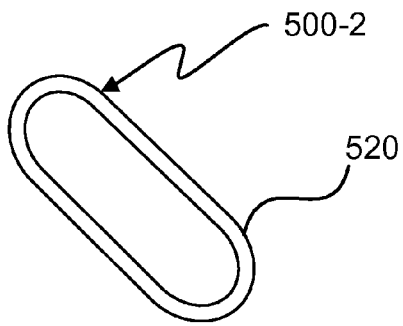
Figure 5C:
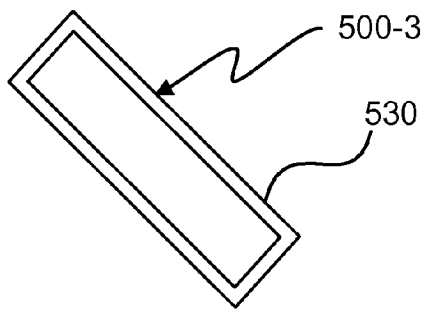
Figure 5D:
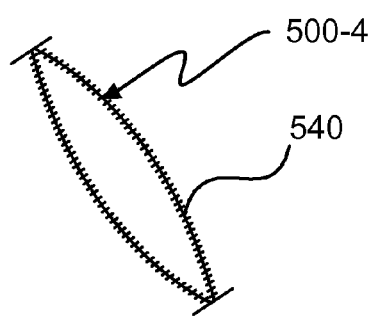
Figure 5E:
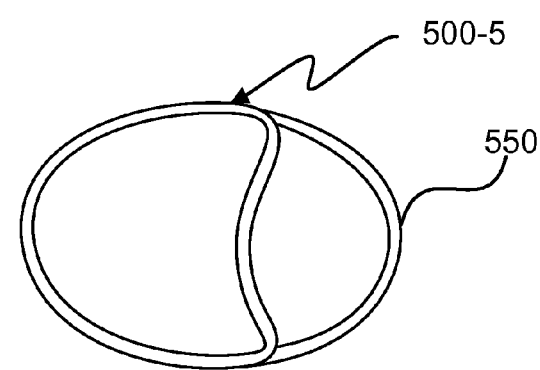

Referring next to FIG. 5A-5E, structural diagrams of embodiments of reinforcement 500 around an opening of the elongated pouch are shown. FIG. 5A shows a round grommet 510; FIG. 5B shows an oval grommet 520; FIG. 5C shows a rectangular grommet 530; FIG. 5D shows a buttonhole reinforcement 540; FIG. 5E shows a guiding reinforcement 550. The reinforcement 500 prevents the cloth opening from tearing and/or separating from the reinforcement 500.

The reinforcement 500 also guides the tube assembly 130 into and/or out of the elongated pouch 110 such that the tube assembly 130 is oriented and/or pointed to a direction away from the wearer's face and/or neck. When the wearer wears the sweatshirt 100 or the jacket 300, it is desirable that the portion of the tube assembly 130 that is outside the elongated pouch 110 points away from the user's head or neck. The portion of the tube assembly 130 that is outside the elongated pouch 110 is referred to as an outside portion 132 of the tube assembly 130; the portion of the tube assembly 130 that is inside the elongated pouch 110 is referred to as an inside portion 134 of the tube assembly 130. The reinforcements 500 allow the outside portion 132 of the tube assembly 130 to be oriented at any desirable angle with respect to the inside portion 134 of the tube assembly 130.

For example, in the embodiments shown in FIGS. 1A-1D, the outside portion 132 of the tube assembly 130 is oriented substantially along and/or parallel to the extension of the inside portion 134 of the tube assembly 130. When the hood 104 is pulled back, or in the embodiments shown FIGS. 3A-3E, the outside portion 132 of the tube assembly 130 is bent toward perpendicular with respect to the inside portion 134 of the tube assembly 130. Depending on how the wearer is wearing the sweatshirt 100 or the jacket 300, the outside portion 132 and the inside portion 134 of the tube assembly 130 can form any suitable angles in the range of zero to 90 degrees, such as about 80, 75, 60, 45, 30, 15 degrees, or less.

Figure 6A:
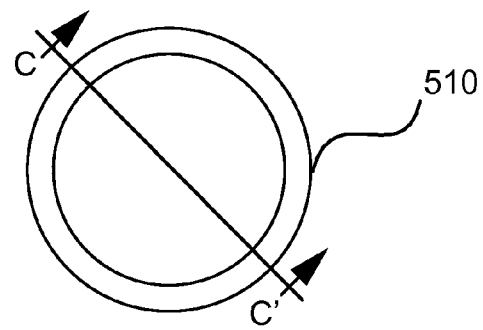
FIG. 6A illustrates a plan view of the reinforcement of FIG. 5A.
Figure 6B:
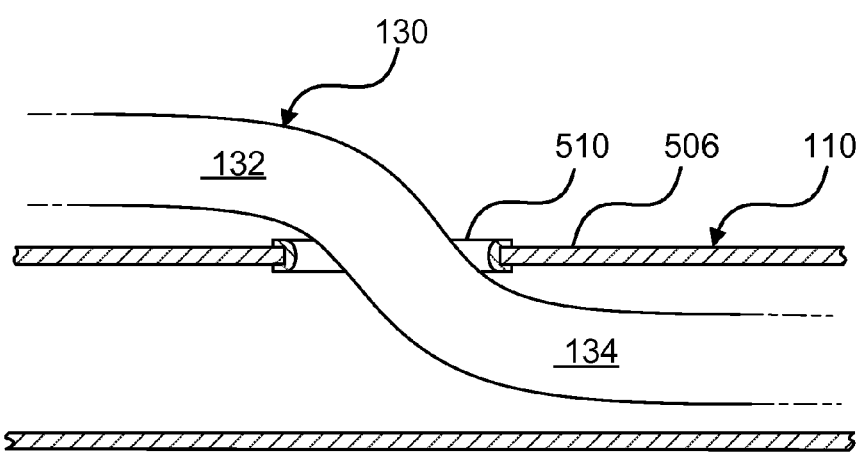
FIG. 6B illustrates a cross-sectional view of the reinforcement of FIG. 5A, viewed along line C-C' of FIG. 6A.

With reference to FIG. 6B, a cross-sectional view of the round grommet 510, viewed along line C-C' of FIG. 6A, is shown. The tube assembly 130 and the adjacent fabric 506 are also shown. The round grommet 510 is flared on either side of the fabric 506 and sandwiches or clamps the edge of the fabric 506 to prevent tearing. An inner diameter of the round grommet 510 defines the opening of the elongated pouch 110. The inner diameter of the round grommet 510 is no less than 0.6, 0.8, 1, 1.2, 1.4, 1.6, 1.8, or 2 centimeters and/or no less than 1, 1.2, 1.4, 1.6, 1.8, or 2 times an outer diameter of the tube assembly 130. When the tube assembly 130 is tread through the round grommet 510, the outside portion 132 of the tube assembly 130 can be transitioned into any suitable orientation with respect to the inside portion 134 of the tube assembly 130.

Figure 7A:
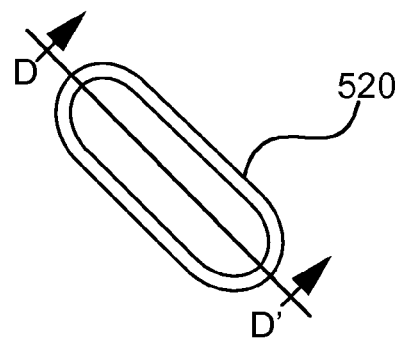
FIG. 7A illustrates a plan view of the reinforcement of FIG. 5B.
Figure 7B:
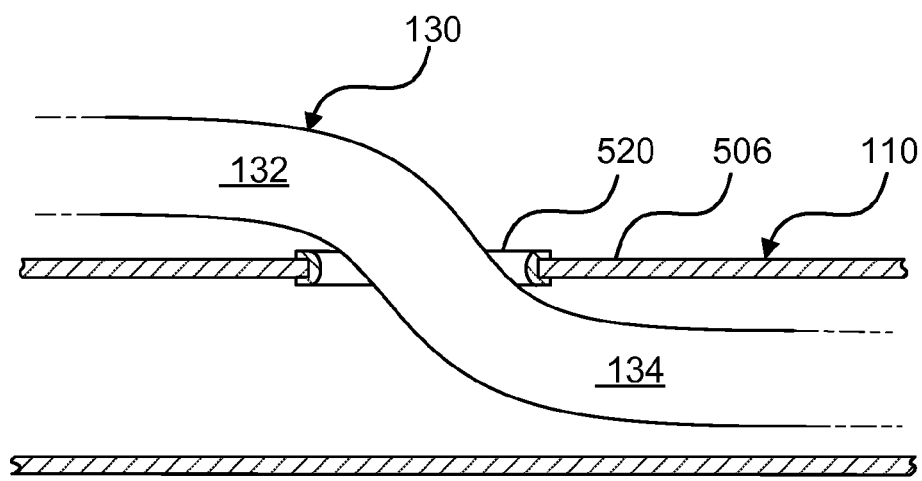
FIG. 7B illustrates a cross-sectional view of the reinforcement of FIG. 5B, viewed along line D-D' of FIG. 7A.

With reference to FIG. 7B, a cross-sectional view of the oval grommet 520, viewed along line D-D' of FIG. 7A, is shown. The tube assembly 130 and the adjacent fabric 506 are also shown. The oval grommet 520 defines an elongated opening. The elongated opening has a width dimension that is close to, or slightly greater than, the outer diameter of the tube assembly 130. The elongated opening has a length dimension that is much greater than the outer diameter of the tube assembly 130. In some embodiments, the width dimension of elongated opening is no less than 1, 1.1, 1.3, 1.5, 1.7, 1.9, or 2 times the outer diameter of the tube assembly 130. The length dimension of the elongated opening is no less than 1.4, 1.6, 1.8, 2, 2.2, 2.4, 2.6, 2.8, 3, 3.5, or 4 times the outer diameter of the tube assembly 130.

When the oval grommet 520 is affixed to the elongated pouch 110, the length dimension of the elongated opening is oriented substantially parallel to the extension of an adjacent portion of the inside portion 134 of the tube assembly 130. This way, the outside portion 132 of the tube assembly 130 can be oriented at any suitable angle with respect to the inside portion 134 of the tube assembly 130. For example, as shown in FIG. 7B, the outside portion 132 and the inside portion 134 are substantially parallel to each other. In other embodiments, the outside portion 132 of the tube assembly 130 can be oriented at different angles, ranging from 0 to 15, 30, 45, 60, 75, or 90 degrees. The elongated opening allows the outside portion 132 of the tube assembly 130 to extend along the surface of the garment and/or to point away from the wearer's face and/or neck in one embodiment.

Although not shown in the drawings, the rectangular grommet 530 and the buttonhole reinforcement 540 also allows the outside portion 132 of the tube assembly 130 to point away from the wearer's face and/or neck. As shown in FIGS. 5C and 5D, the rectangular grommet 530 and the buttonhole reinforcement 540 each also define an elongated opening. The respective elongated openings allow the outside portion 132 of the tube assembly 130 to be oriented at any suitable angle with respect to the inside portion 134 of the tube assembly 130. Depending on the design of the garment (e.g., the sweatshirt 100 and/or the jacket 300) and/or the location of the reinforcements 500, the elongated openings of the reinforcements 500 can be positioned vertically, horizontally, or in any suitable orientation.

Figure 8A:
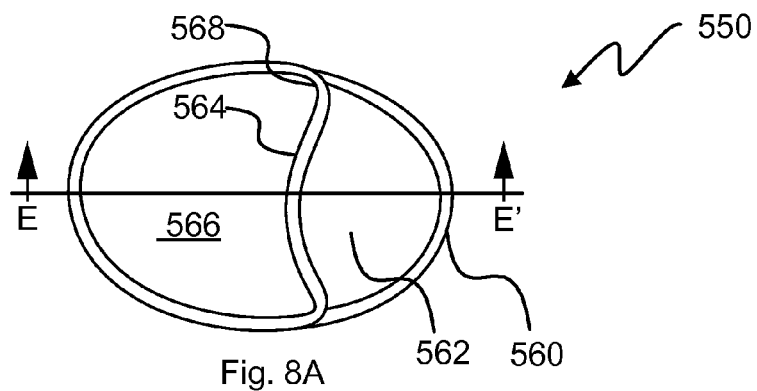
FIG. 8A illustrates a plan view of the reinforcement of FIG. 5E.
Figure 8B:
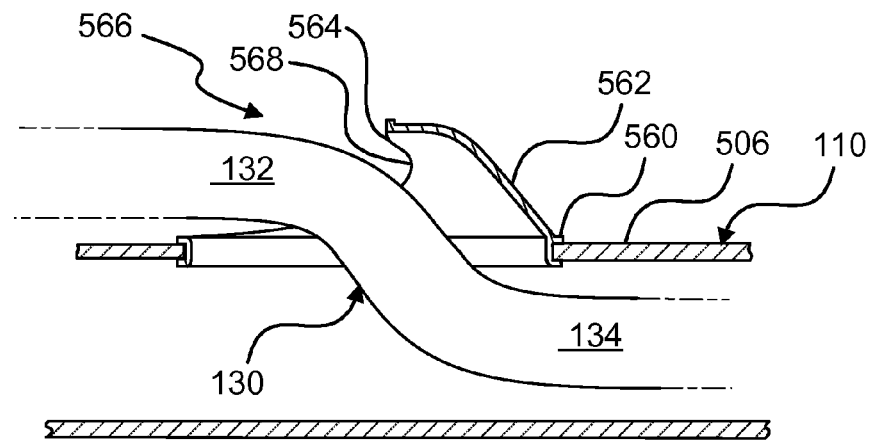
FIG. 8B illustrates a cross-sectional view of the reinforcement of FIG. 5E, viewed along line E-E' of FIG. 8A.

With reference to FIG. 8B, a cross-sectional view of the guiding reinforcement 550, viewed along line E-E' of FIG. 8A, is shown. The tube assembly 130 and the adjacent fabric 506 are also shown. The guiding reinforcement 550 extends outward from a plane defined by the fabric 506 to guide the tube assembly 130 tangentially with respect to the plane.

The guiding reinforcement 550 includes a reinforcing grommet 560 and a cover, partial dome, or elbow-shaped shell 562. The reinforcing grommet 560 is positioned around the opening of the fabric 506 to prevent tearing or separation of the fabric 506 from the reinforcing grommet 560. The reinforcing grommet 560 has an oval shape in this embodiment, but could be formed of circular, triangular, rectangular, trapezoidal, oval, diamond, or any suitable shapes. The elbow-shaped shell 562 extends outward from the reinforcing grommet 560 and extends over a portion of the opening defined by the reinforcing grommet 560. A shell leading edge 564 of the elbow-shaped shell 562 defines a guiding outlet 566 for the tube assembly 130.

In this embodiment, the elbow-shaped shell 562 extends over or traverses about 40% the longitudinal axis of the reinforcing grommet 560. In some embodiments, the elbow-shaped shell 562 extends over at least 20%, 30%, 50%, 60%, 70%, 80%, or 90% of the longitudinal axis of the reinforcing grommet 560. The shell leading edge 564 has a contoured profile. For example, the shell leading edge 564 includes side portions 568 that curve backward to make it easier to pull the outside portion 132 towards, for example, the wearer's mouth.

The reinforcing grommet 560 and the elbow-shaped shell 562 cooperatively guide and/or orient the tube assembly 130. In the embodiment shown in FIG. 8B, the outside portion 132 of the tube assembly 130 is guided to extend along the outer surface of the fabric 506. The inside portion 134 of the tube assembly 130 extends along the elongated pouch 110 and thus extends along the inner surface of the fabric 506. In this embodiment, the outside portion 132 and the inside portion 134 of the tube assembly 130 are substantially parallel to each other. Depending on the design of the garment, the outside portion 132 566 and the inside portion 134 of the tube assembly 130 can be guided to form any suitable angles.

Figure 8C:
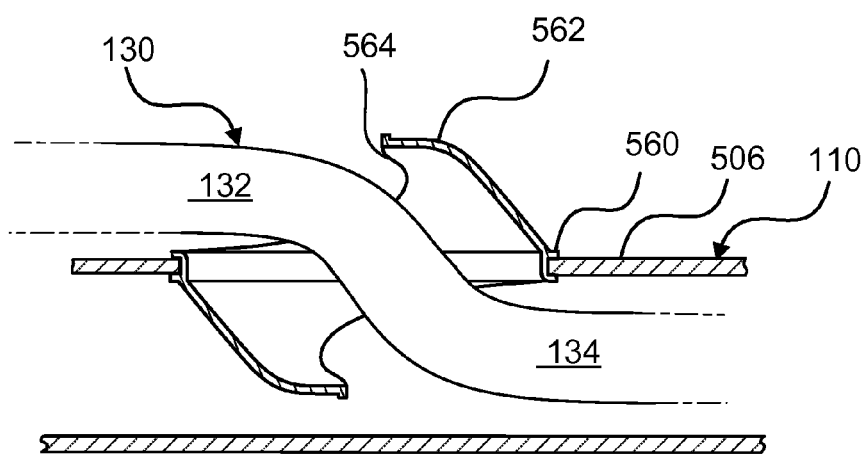
FIG. 8C illustrates a cross-sectional view of another embodiment of reinforcement around the opening of the elongated pouch.

With reference to FIG. 8C, a cross-sectional view of another embodiment of reinforcement 500-6 around an opening of the elongated pouch 110 is shown. The reinforcement 500-6 is formed by joining two guiding reinforcements 550 at the opening of the elongated pouch 110. Specifically, the two guiding reinforcements 550 are oriented opposite to each other and are joined at their respective reinforcing grommets 560. The second/additional guiding reinforcement 550 is thus positioned inside the elongated pouch 110. The elbow-shaped shell 562 of the second/additional guiding reinforcement 550 guides the inside portion 134 of the tube assembly 130 to substantially extend along the inner surface of the fabric 506.

The two guiding reinforcements 550 can be joined by gluing, welding, snap-fit, riveting, clamping, and/or any suitable connecting mechanism. In some embodiments, the reinforcement 500-6 can be formed as a unitary piece. This embodiment shows the two guiding reinforcements 550 are structured the same but oriented oppositely. In some embodiments, the elbow-shaped shell 562 outside the elongated pouch 110 and the elbow-shaped shell 562 inside the elongated pouch 110 can be sized and/or shaped differently.

Figures 9A, 9B:
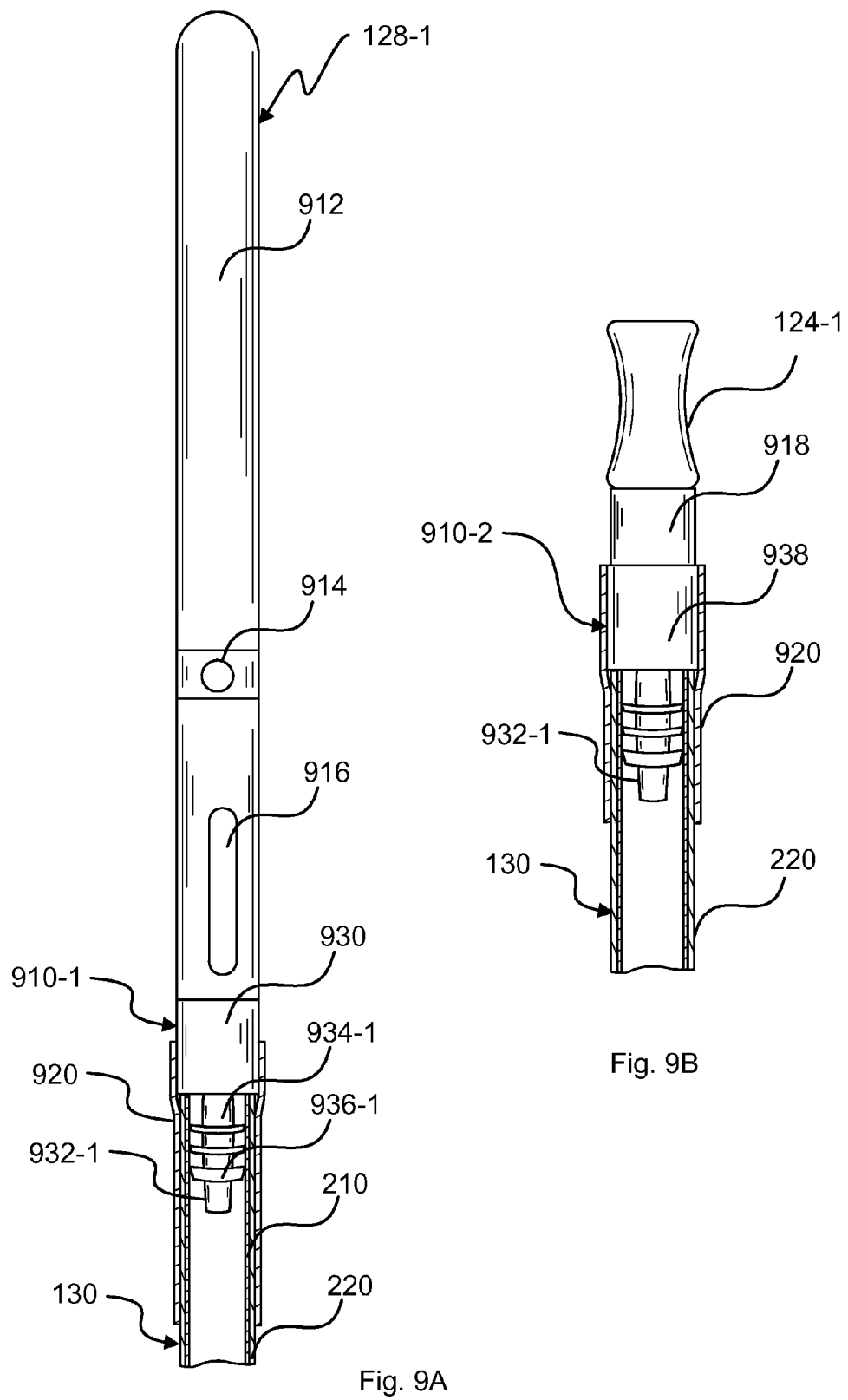
FIG. 9A illustrates an embodiment of an adaptor connecting the liquid encapsulating device to a tube assembly.
FIG. 9B illustrates one embodiment of the adaptor connecting a mouthpiece to the tube assembly.

With reference to FIG. 9A, an embodiment of a liquid encapsulating device, vapor pen or vaporizing device 128-1 is shown. The vaporizing device 128-1 is removably attached to the end of the tube assembly 130 by a female adaptor 910-1. With reference to FIG. 9B, an embodiment of a mouthpiece 124-1 is shown. The mouthpiece 124-1 is removably attached to the end of the tube assembly 130 by a male adaptor 910-2.

The vaporizing device 128-1 includes a power source or battery compartment 912, an activation switch 914, a vapor chamber or heating chamber 916, a male connector 922 (shown in FIG. 9C), and a vapor outlet (not shown). The vaporizing device 128-1 has a general cylindrical shape with a diameter of no more than 0.8, 1, 1.2, 1.4, 1.6, 1.8, 2, 2.4, or 2.6 centimeters in various embodiments. In some embodiments, the vaporizing device 128-1 has a contoured shape with a varying diameter along its longitudinal dimension.

The mouthpiece 124-1 includes a female connector 918 at one end of the mouthpiece 124-1. The female connector 918 of the mouthpiece 124-1 and the male connector 922 of the vaporizing device 128-1 mate with each other. For example, the male connector 922 of the vaporizing device 128-1 includes external threading, and the female connector 918 of the mouthpiece 124-1 includes internal threading that is opposite to the external threading of the male connector 922 of the vaporizing device 128-1. Thus, the mouthpiece 124-1 can be screwed onto and/or unscrewed from the vaporizing device 128-1.

To connect the mouthpiece 124-1 and the vaporizing device 128-1 to the ends of the tube assembly 130, the female and male adaptors 910-1, 910-2 also include opposite, mating threading. With reference to FIG. 9A, the female adaptor 910-1 includes a receptacle 930 at one end to connect with the vaporizing device 128-1 and a tube fitting 932-1 at the other end. The receptacle 930 includes internal threading that mates with the external threading of male connector 922 of the vaporizing device 128-1. As such, the vaporizing device 128-1 can be removably attached to the tube assembly 130 by the female adaptor 910-1. The tube fitting 932-1 includes a stem 934-1 and ridges 936-1 around the stem 934-1. The stem 934-1 includes a center bore (not shown) for passing through fluidal or vaporized material. The ridges 936-1 creates an interference fit or friction fit between the tube fitting 932-1 and the tube inner layer 210. To further secure the female adaptor 910-1 to the tube assembly 130, a shrink tubing 920 is place around the joint between the female adaptor 910-1 and the tube assembly 130.

With reference to FIG. 9B, the male adaptor 910-2 include the tube fitting 932-1, a tightening body 938, and an externally threaded portion (not shown). The tightening body 938 has the same exterior diameter as that of the receptacle 930 of the female adaptor 910-1. The externally threaded portion is sized and threaded for mating with the female connector 918 of the mouthpiece 124-1. As such, the externally threaded portion of the male adaptor 910-2 also fits inside the receptacle 930 of the female adaptor 910-1. The two ends of the tube assembly 130 thus can be screwed together by the adaptors 910 when not used to prevent external elements, such as dust, moisture, etc., from getting inside the tube assembly 130.

Depending on the threading configuration of the particular mouthpiece 124 and the vaporizing device 128, in some embodiments, the female adaptor 910-1 is removably connected to the mouthpiece 124 and the male adaptor 910-2 is removably connected to the vaporizing device 128. In one embodiment, the adaptors 910 are made of silicone, but the adaptors 910 can be made of plastic, rubber, wood, ceramic, metal, and/or any suitable material. The adaptors 910 are formed as a unitary piece by molding (e.g., injection molding), 3-D printing, or any suitable fabrication/manufacturing process.

Figures 9C, 9D:
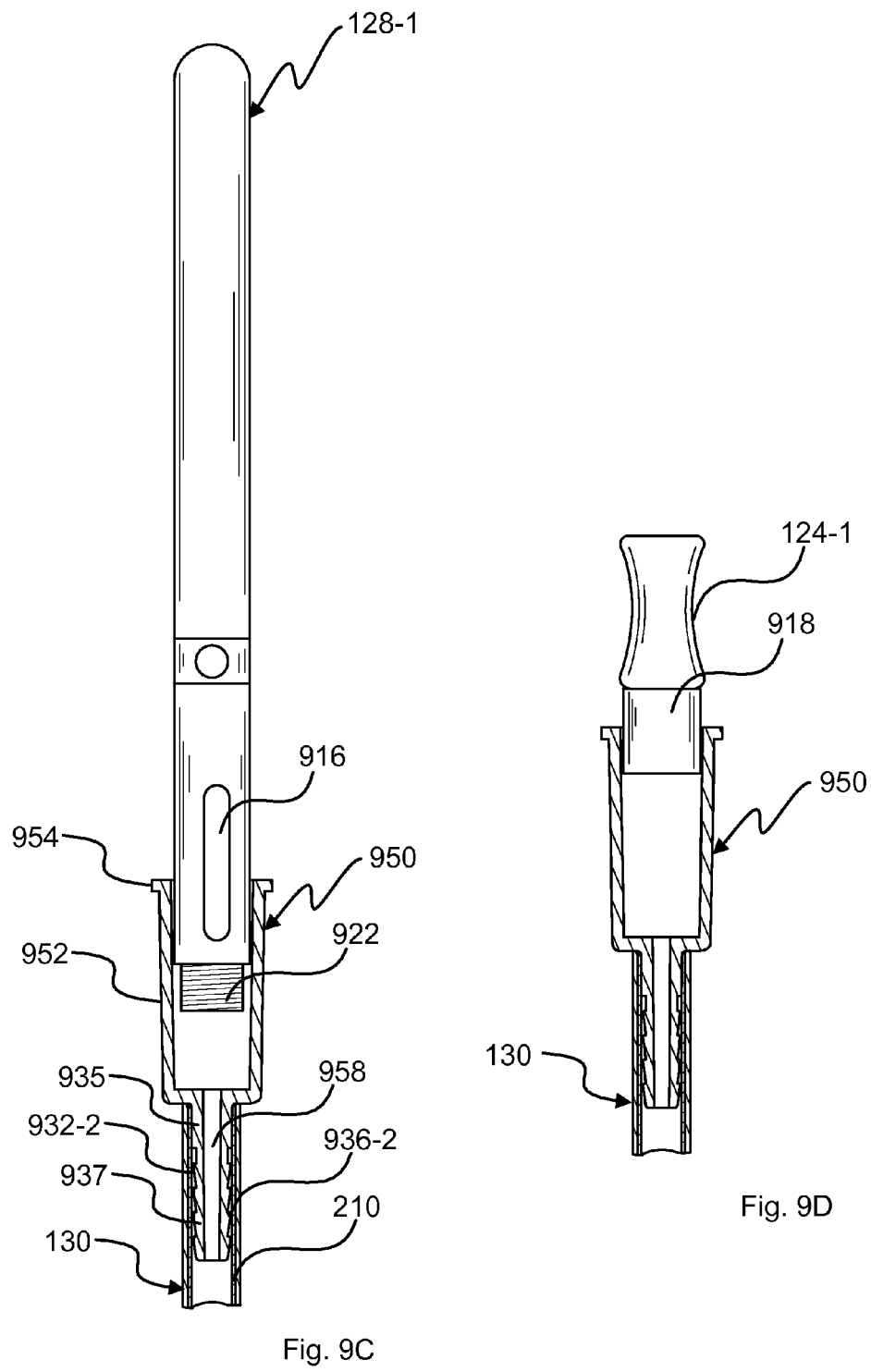
FIG. 9C illustrates one embodiment of the adaptor connecting the liquid encapsulating device to the tube assembly.
FIG. 9D illustrates the adaptor of FIG. 9C connecting a mouthpiece to the tube assembly.
Figure 9E:
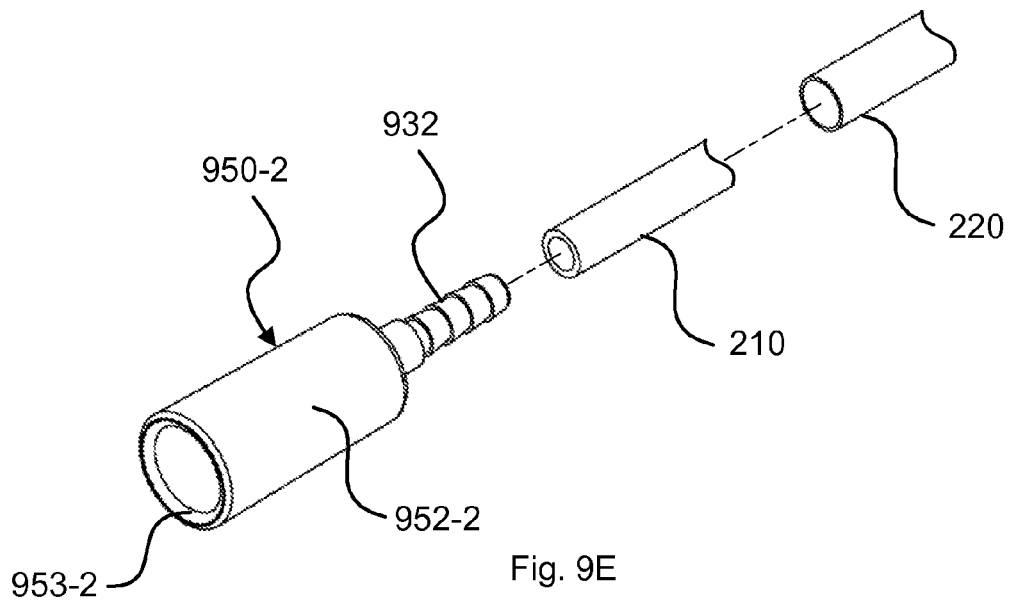
FIG. 9E illustrates a perspective view of one embodiment of the adaptor and an end portion of the tube assembly where various parts are shown in an exploded view.

With reference to FIG. 9C, a cross-sectional view of an embodiment of a universal adaptor 950 for removably attaching the vaporizing device 128-1 to the tube assembly 130 is shown. FIG. 9D shows the mouthpiece 124-1 being removably attached to the tube assembly 130 by the universal adaptor 950. The universal adaptor 950 includes a universal receptacle 952 and a tube fitting 932-2. The universal receptacle 952 receives an end of the vaporizing device 128-1 or the mouthpiece 124-1. The tube fitting 932-2 fits inside the tube assembly 130. The outer diameter of the universal receptacle 952 is greater than the outer diameter of the tube assembly 130. As such, the universal adaptor 950 resembles a funnel.

In some embodiments, the universal receptacle 952 is substantially cylindrically shaped. In some embodiments, the universal receptacle 952 includes a slightly tapered end that forms a slightly enlarged opening to facilitate insertion of the vaporizing device 128 and/or the mouthpiece 124-1. The tapered end is reinforced by a flange 954. With reference to FIG. 9C, the male connector 922 of the vaporizing device 128-1 and an adjacent portion of the heating chamber 916 are received inside (or pushed into) the universal receptacle 952. The vaporizing device 128-1 is held inside the universal receptacle 952 by friction.

The tube fitting 932-2 includes a base portion 935, a ridged portion 937, and a center bore 958 for passing through fluidal or vaporized material. The base portion 935 is substantially cylindrically shaped. An outer diameter of the base portion 935 substantially corresponds to the inner diameter of the tube inner layer 210 so as to form a tight fit inside the tube inner layer 210. The ridged portion 937 includes circumferentially formed ridges 936-2. As shown in FIGS. 9C and 9D, the ridges 936-2 are directional so as to allow easy insertion into the tube assembly 130 but limit and/or prevent reverse motion (i.e., sliding out of the tube assembly 130).

In one embodiment, the universal adaptor 950 is made of silicone, but the universal adaptor 950 can be made of plastic, rubber, wood, ceramic, metal, and/or any suitable material. The universal adaptor 950 can be formed as a unitary piece by molding (e.g., injection molding), 3-D printing, or any suitable fabrication/manufacturing process. In some embodiments, the interior of the universal receptacle 952 can withstand a slight deformation to snugly fit over the mouthpiece 124 and/or the vaporizing device 128 without causing any scratches or damages. If the universal adaptor 950 is formed with a relatively rigid material (e.g., metal, ceramic, etc.) for structural strength, the universal receptacle 952 can optionally include a lining formed with a relatively soft material (e.g., rubber, plastic, wood, etc.).

Figure 9F:
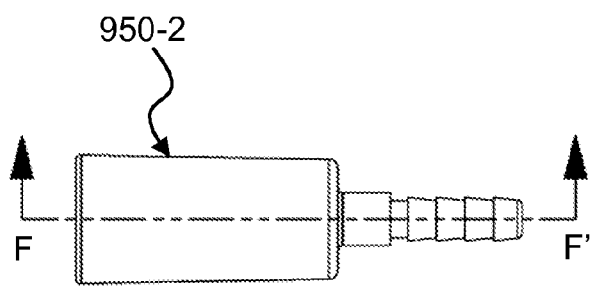
FIG. 9F illustrates a plan view of the adaptor of FIG. 9E.
Figure 9G:
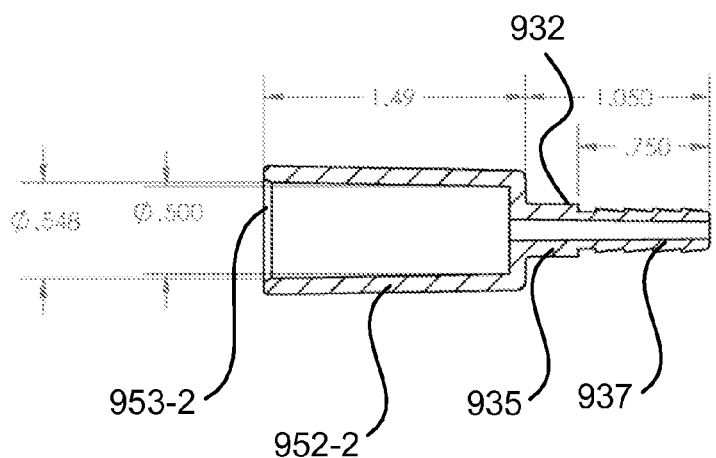
FIG. 9G illustrates a cross-sectional view of the adaptor of FIGS. 9E and 9F, viewed along line F-F' of FIG. 9F.

With reference to FIG. 9E-9J, various views of other embodiments of the universal adaptor 950 for removably attaching the vaporizing device 128 and/or the mouthpiece 124 to the tube assembly 130 are shown. FIG. 9F is a plan view of the adaptor 950-2 of FIG. 9E. FIG. 9G is a cross-sectional view of the adaptor of FIG. 9F, viewed along line F-F'. FIG. 9I is a plan view of the adaptor 950-3 of FIG. 9H. FIG. 9J is a cross-sectional view of the adaptor of FIG. 9I, viewed along line G-G'. In these embodiments, the tapered end of the universal receptacle 952-2, 952-3 is further tapered to form a rounded or beveled edge 953-2, 953-3. The rounded or beveled edge 953-2, 953-3 facilitates the insertion of the vaporizing device 128 and/or the mouthpiece 124.

FIGS. 9G and 9J indicate the dimensions of the respective universal adaptors 950 in inches. With reference to FIGS. 9G and 9J, the tube fitting 932 has a length of about 1 inch. The ridged portion 937 is about 3 times the length of the base portion 935. In various embodiments, the length of the tube fitting 932 can be no less than 0.5, 0.7, 0.9, 1.1, 1.3, 1.5, 1.7, 1.9, 2 inches or any other suitable dimensions. The ridged portion 937 can be 0.25, 0.5, 0.75, 1, 2, 4, 5, or 6 times the length of the base portion 935. In some embodiments, the tube fitting 932 may not include the base portion 935 and only include the ridged portion 937, or vice versa. The universal receptacle 952 has a length or a depth of about 1.5 inches. In various embodiments, the universal receptacle 952 can be longer or shorter. The length of the universal receptacle 952 is no less than 0.5, 0.75, 1, 1.25, 1.5, 1.75, 2, 2.5, or 3 times the length of the tube fitting 936.

With further reference to FIG. 9G, the inner diameter of the universal receptacle 952-2 near the tapered end is about 0.55 inch, and the inner diameter of the universal receptacle 952-2 near the base of the universal receptacle 952-2 is about 0.5 inch. With further reference to FIG. 9J, the inner diameter of the universal receptacle 952-3 near the tapered end is about 0.35 inch, and the inner diameter of the universal receptacle 952-3 near the base of the universal receptacle 952-3 is about 0.25 inch. In various embodiments, the universal receptacle 952 can have other inner diameter dimensions near the base and/or the tapered end, ranging from 0.1 to 0.5 inches.

In some embodiments, the inner diameter dimensions of the universal receptacle 952 are relatively small, the universal receptacle 952 is therefore more tapered. In some embodiments, the inner diameter dimensions of the universal receptacle 952 are relatively large, then the universal receptacle 952 is less tapered. For example, comparing the embodiment of FIG. 9G and FIG. 9J, the universal receptacle 952-2 of FIG. 9G is wider than the universal receptacle 952-3 of FIG. 9J. The universal receptacle 952-2 of FIG. 9G is also less tapered than the universal receptacle 952-3 of FIG. 9J. In various embodiments, the inner diameter of the universal receptacle 952 near the taper end can be 5%, 10%, 15%, 20%, 30%, 40%, 50%, 60%, 70%, or 80% greater than the inner diameter of the universal receptacle 952 near the base.

The universal adapter 950 could have an integral one-way valve or p-trap. Under some circumstances, condensation can accumulate in the tube inner layer 210 and flow back into the vaporizing device 128. The one-way valve prevents the liquid condensation from returning into the vaporizing device 128. A flap is used in one embodiment to prevent return of liquid into whatever technology is inserted into the universal adapter 950. The flap or the integral one-way valve can be positioned at the tip or distal end of the tube fitting 932 or at any suitably location along the center bore 958 of the tube fitting 932. In some embodiments, the center bore 958 can be suitably sized or include surface treatment such that fluidal or vaporized material will only pass the center bore 958 when a user inhales the fluid or vaporized material from the other end of the tube assembly 130. The center bore 958 may include a diameter of no greater than 0.05, 0.075, 0.1, 0.125, 0.15, 0.175, or 0.2 inches.

Figure 9K:
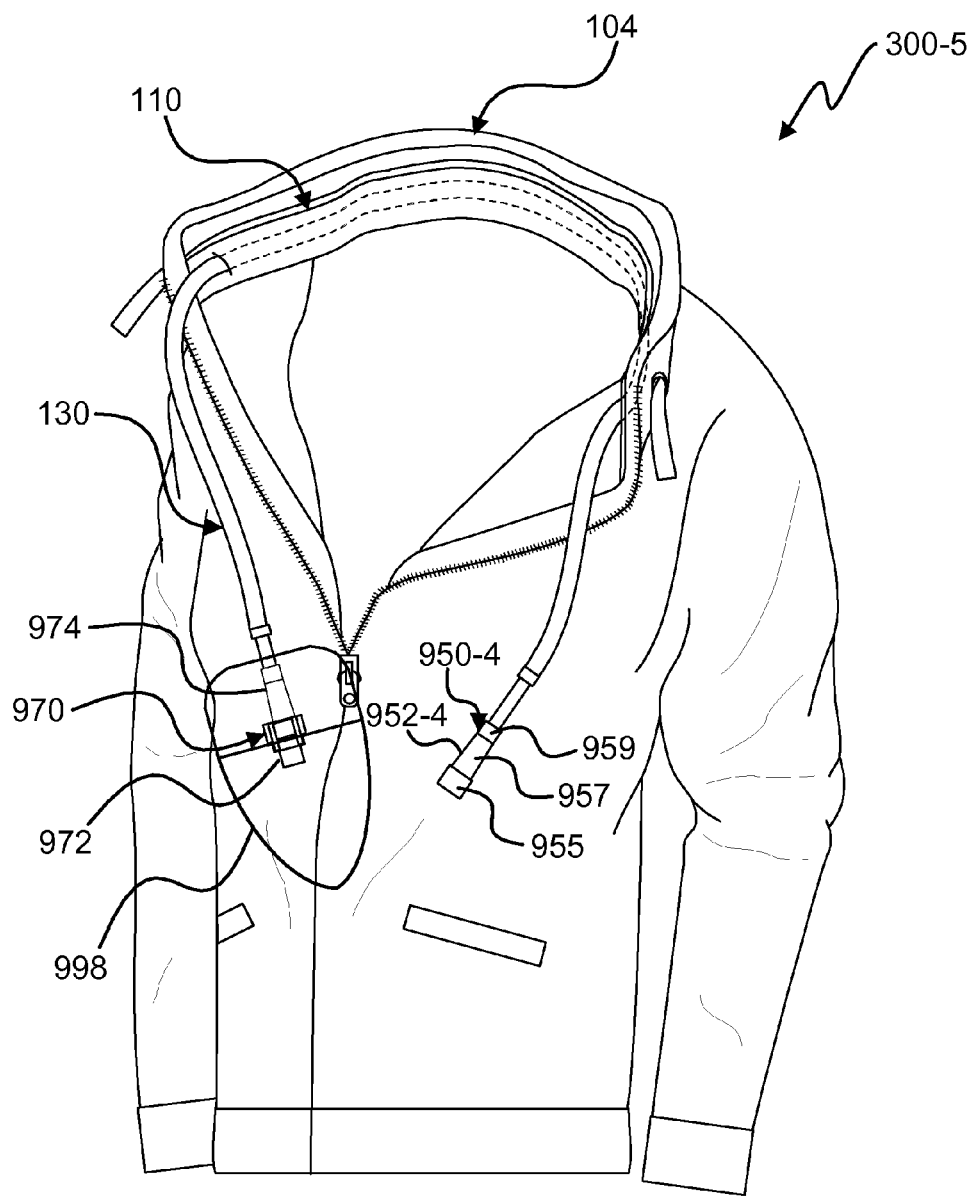
FIG. 9K illustrates the body-top garment and the tube assembly, with another embodiment of the adaptor attached to the ends of the tube assembly.

With reference to FIG. 9K, a body-top garment or jacket 300-5 similar to that described above with reference to FIGS. 3A-3E is shown. The jacket 300-5 houses a portion of the tube assembly 130 in the elongated pouch 110 along the collar 104 of the jacket 300-5. Another embodiment of the universal adaptor 950-4 is attached to either end of the tube assembly 130. The universal receptacle 952-4 of the universal adaptor 950-4 includes: a tapered portion 957, a substantially cylindrically-shaped end portion 955 joined to the wider end of the tapered portion 957, a substantially cylindrically shaped base portion 959 joined to the narrower end of the tapered portion 957, and the tube fitting 936 (not shown) joined to the base end portion 959. The substantially cylindrically-shaped end portion 955 attaches to an oxygen generator or tank (not shown).

One of the universal adaptors 950-4 is connect to a mask connector 970 attached to a face mask 998. The mask connector 970 includes an adaptor-connecting member 974 for coupling with the universal adaptor 950-4 and a mask-connecting member 972 for coupling with a mask, such as an oxygen mask. The adaptor-connecting member 974 includes a tubing member (not shown). The tubing member is in fluid communication with the mask-connecting member 972. The tubing member is fitted inside the universal adaptor 950-4 to establish communication between the mask and the tube assembly 130. The mask-connecting member 972, the adaptor-connecting member 974, and/or the tubing member are formed as one unitary piece in some embodiments, but can be formed as separate pieces and assembled together to form the mask-connector 970.

Figure 9L:
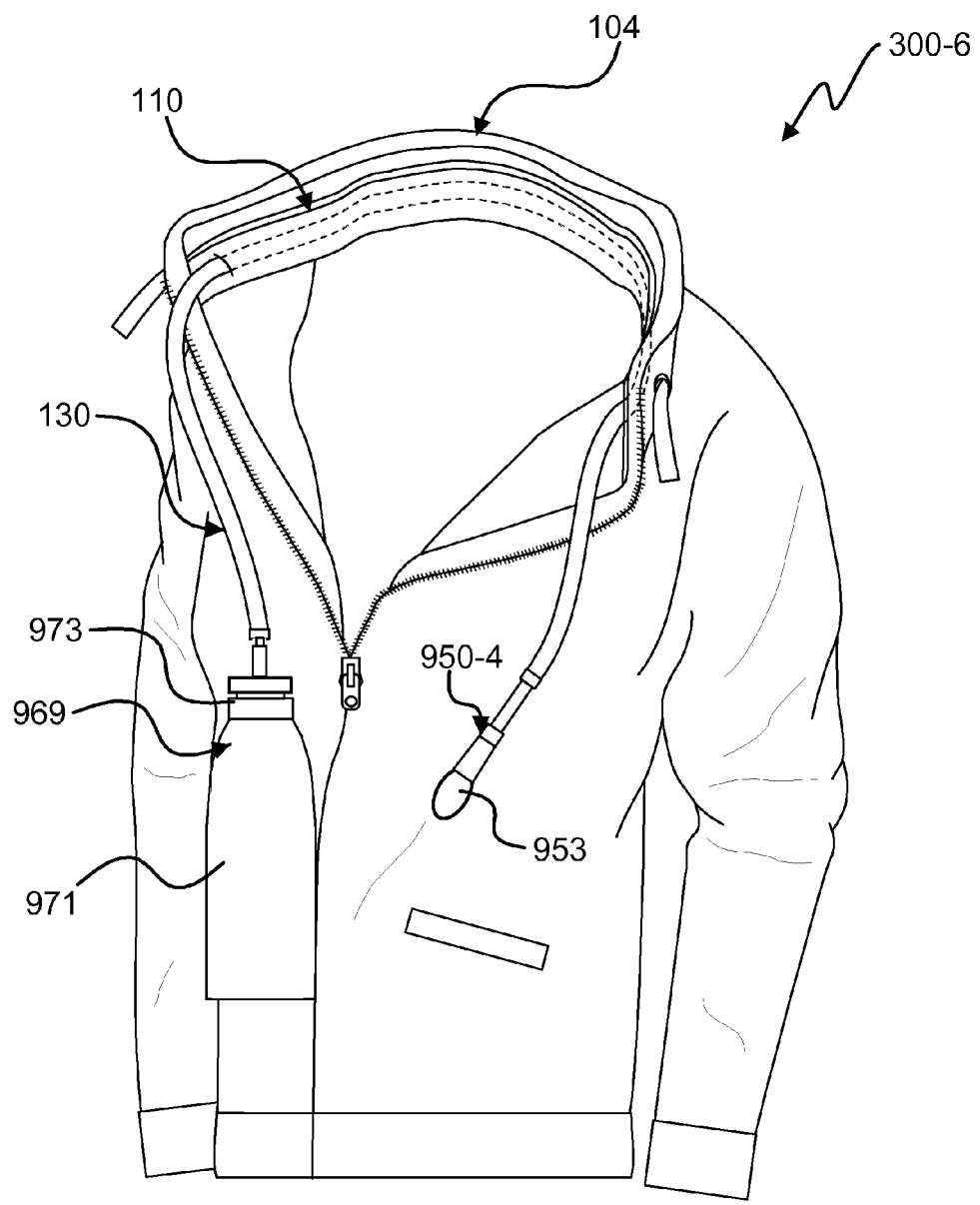
FIG. 9L illustrates the body-top garment and the tube assembly configured for oxygen delivery.

With reference to FIG. 9L, a body-top garment or jacket 300-6 similar to that described above with reference to FIGS. 3A-3E is shown. This embodiment has an oxygen generator 969 with a tank 971 and adapter 973 connected to the tube assembly 130 on one end. The other end of the tube assembly 130 has the universal adapter 950-4 attached to an oxygen valve 953. The oxygen valve could be a bite valve that only lets oxygen flow when bit between the wear's teeth. Other embodiments could only have oxygen flow when the oxygen valve is sucked by the wearer.

Figure 10A:
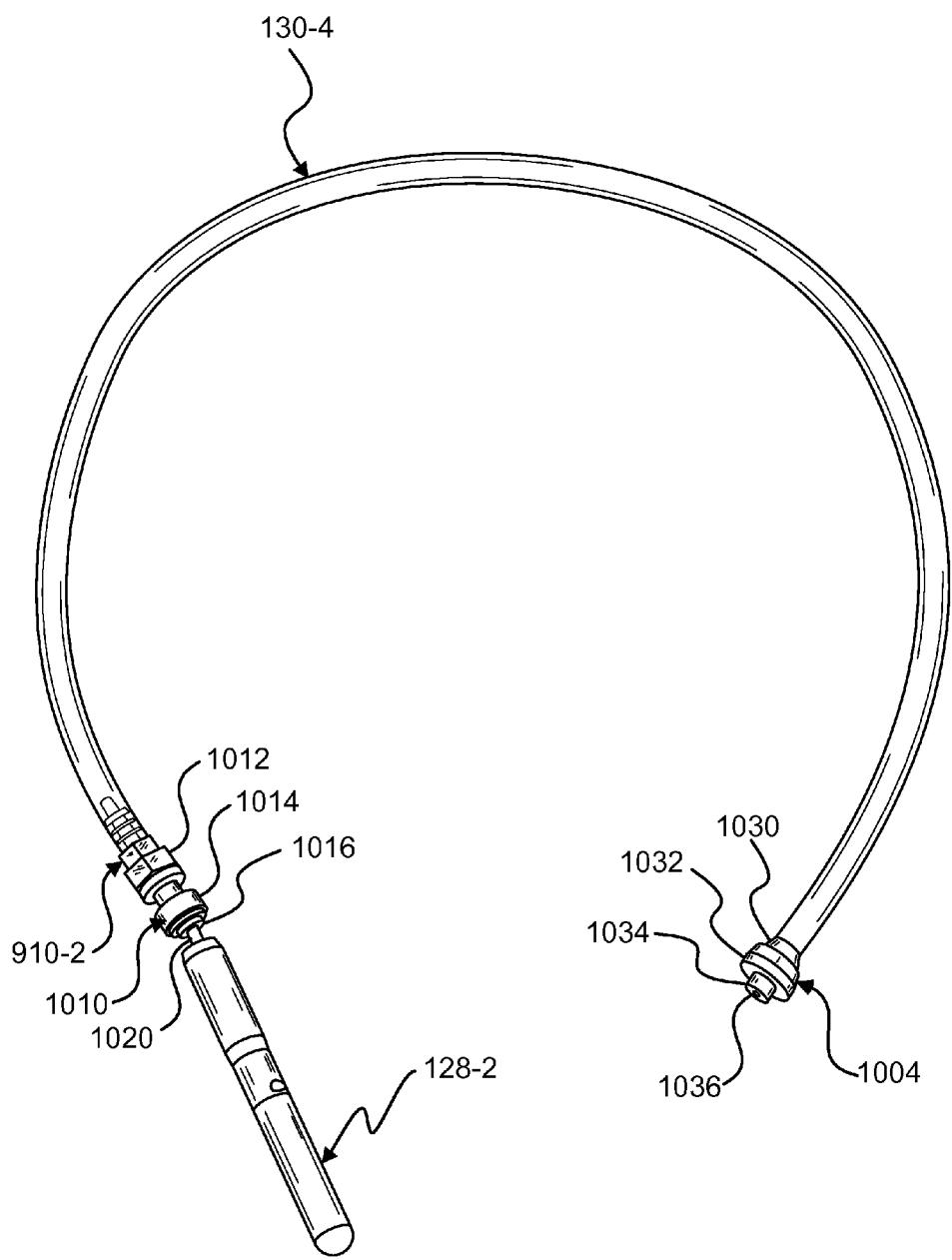
FIGS. 10A-10D illustrate various views of embodiments of the tube assembly with the liquid encapsulating device attached to ends of the tube assembly.

With reference to FIG. 10A, another embodiment of a liquid encapsulating device, vapor pen or vaporizing device 128-2 is shown. In this embodiment, the vaporizing device 128-2 includes an elongated vapor outlet 1020. The vaporizing device 128-2 is connected to one end of the tube assembly 130-4 by the male adaptor 910-2 and a female-to-female adaptor 1010. A tube cap 1004 is connected to the other end of the tube assembly 130-4. The tube assembly 130-4 includes only one tube layer that delivers the fluidal or vaporized material from one end to the other end. The tube layer is made of plastic or rubber and is transparent or semi-transparent, but could be of any color, translucent, or non-transparent in other embodiments.

The female-to-female adaptor 1010 includes an internally threaded end 1012 and a push-fit end 1014. The internally threaded end 1012 receives the externally threaded portion of the male adaptor 910-2. The push-fit end 1014 further includes an elastic fitting element 1016. The elastic fitting element 1016 has an inner diameter that is less than the outer diameter of the elongated vapor outlet 1020. Accordingly, when the elongate vapor outlet 1020 is pushed into the elastic fitting member 1016, the elastic fitting member 1016 fits snugly around the elongated vapor outlet 1020 and securely attaches the vaporizing device 128-2 to the tube assembly 130. The snug fit between the elastic fitting element 1016 and the elongated vapor outlet 1020 also creates a seal and prevents or limits the fluidal or vaporized material from leaking.

The female-to-female adaptor 1010 can be made of the same material for making the adaptors 910, such as plastic, rubber, wood, ceramic, metal, and/or any suitable material. The elastic fitting member can be made of rubber, plastic, wood, or other suitable materials that can form a tight fit around the elongated vapor outlet 1020.

The tube cap 1004 includes a tube fitting end 1030, a mouthpiece fitting end 1034, and a middle portion 1032 joining the tube fitting end 1030 and the mouthpiece fitting end 1034. A through hole 1036 is formed through the tube fitting end 1030, the middle portion 1032, and the mouthpiece fitting end 1034. The through hole 1036 defines a passage for the fluidal or vaporized material through the tube cap 1004. Because the opening at the end of the tube assembly 130 is reduced to the through hole 1036, dust, moisture, and other external elements are substantially prevented from getting inside the tube assembly 130.

In this embodiment, the tube fitting end 1030 is tapered and forms a frustum. The smaller end of the tube fitting end 1030 is fitted (or pushed) into the tube assembly 130. In some embodiments, the tube fitting end 1030 includes the tube fittings 932 described above with reference to FIGS. 9A-9D for attaching the tube cap 1004 to the tube assembly 130. In some embodiments, the tube cap 1004 and the tube assembly 130 are formed as a unitary piece.

The middle portion 1032 includes a diameter that is greater than the diameter of either the tube fitting end 1030 or the mouthpiece fitting end 1034. In the embodiment of FIG. 9A, the diameter of the middle portion 1032 is further varied along its longitudinal dimension and the middle portion 1032 is formed of two frustums joined at their common base. The two tapered side surfaces of the middle portion 1032 provides gripping surfaces for pushing the tube cap 1004 into the tube assembly 130 and/or pulling the tube cap 1004 out of the tube assembly 130. In other embodiments, the middle portion can be a single frustum, a cylinder, a cubical body, a hexagonal body, or any combinations thereof.

The mouthpiece fitting end 1034 is sized to snugly fit inside the mouthpiece 124. Alternatively, the tube assembly 130-4 is used with only the tube cap 1004 and without the mouthpiece 124. The fluidal or vaporized material can be inhaled or consumed directly from the mouthpiece fitting end 1034.

Figure 10B:
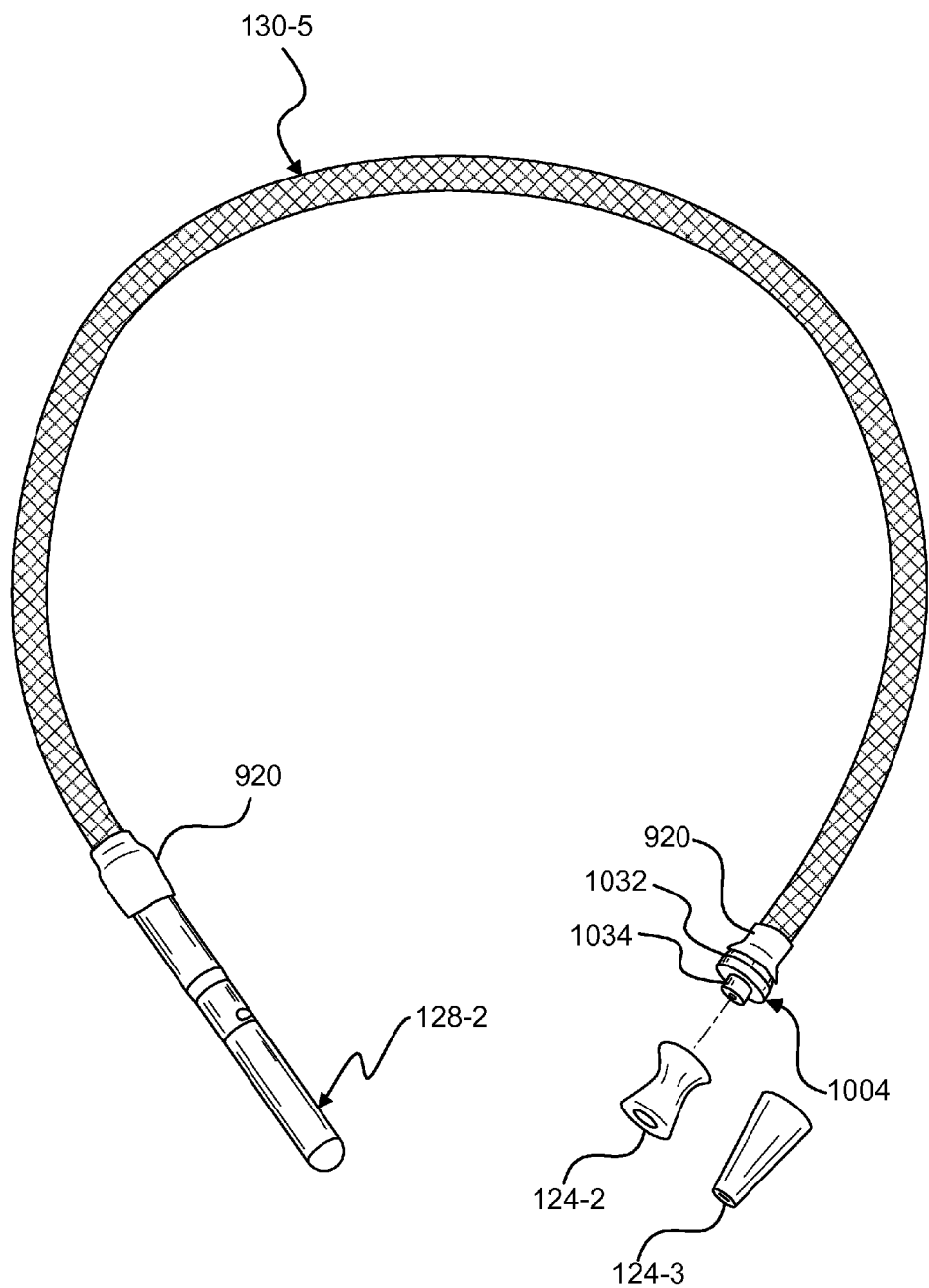

With reference to FIG. 10B, the vaporizing device 128-2 is connected to a different embodiment of the tube assembly 130-5. Two embodiments of the mouthpiece 124-2, 124-3 are also shown. The mouthpiece 124-2 has a contour that resembles an hour glass. The mouthpiece 124-3 has a contour that generally represents a frustum. Other embodiments of mouthpiece 124 that has various contours and/or shapes can be used. To connect the mouthpiece 124 to the tube assembly 130, the mouthpiece fitting end 1034 of the tube cap 1004 is fitted into the center bore of the mouthpiece 124. The mouthpiece 124 is pressed to abut the middle portion 1032 of the tube cap 1004 and held in place by the friction fit between the mouthpiece fitting end 1034 and the mouthpiece 124. In the embodiment shown in FIG. 9B, the tube assembly 130-5 further includes a woven sheath 220. The vaporizing device 128-2 and the tube cap 1004 are each further secured to the tube assembly 130-5 by the shrink tubing 920.

Figure 10C:
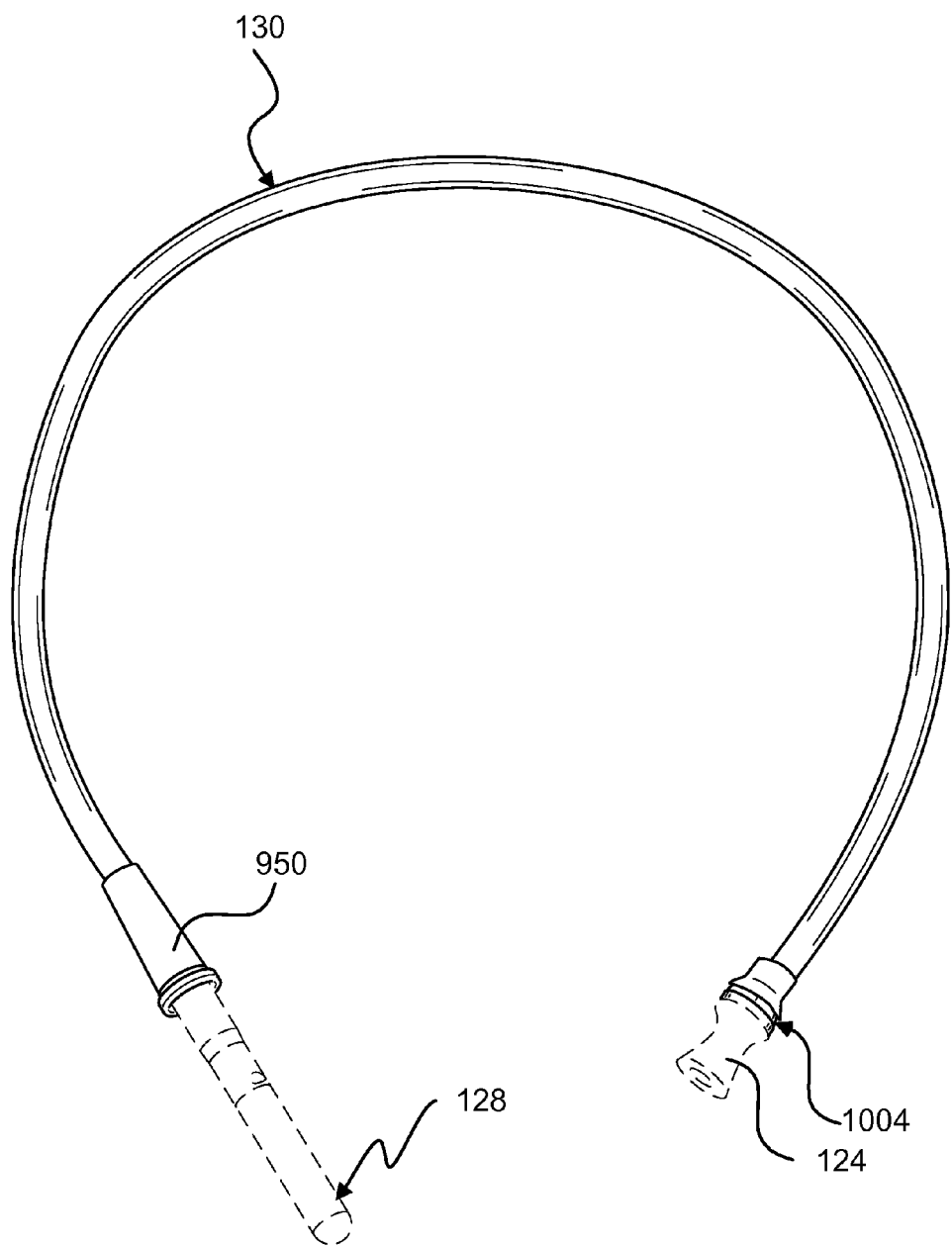

With reference to FIG. 10C, one end of the tube assembly 130 is connected with the universal adaptor 950 similar to that described with reference to FIGS. 9C-9D, and the other end of the tube assembly 130 is connected with a tube cap 1004. A variety of technologies, including but not limited to, the vaporizing device 128, the bladder 310, flask, oxygen generator, the cooperating mouthpieces 124, asthma inhaler, nasal/mouth inhaler, over-the-face/oral/nasal mask, can be attached to the tube assembly 130 via the universal adaptor 950 and the tube cap 1004. This embodiment of the tube assembly 130 is essentially a universally-fitting tube assembly.

Figure 10D:
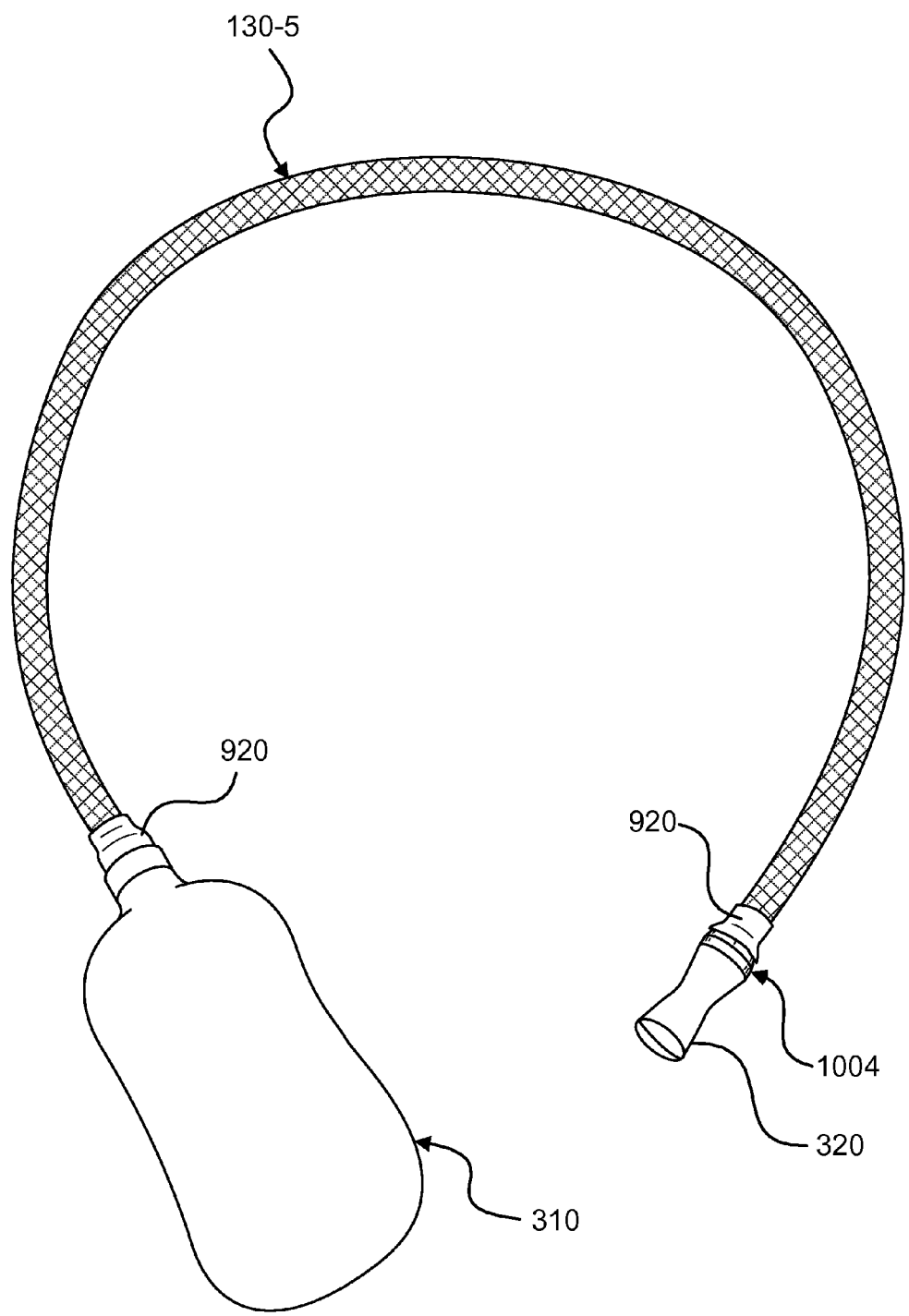

With reference to FIG. 10D, the bladder 310 and the biting valve 320 similar to those described with reference to FIG. 3C above are connected to the tube assembly 130-5. The biting valve is fitted onto the tube cap 1004 and connected to one end of the tube assembly 130-5. The other end of the tube assembly 130-5 is received inside the opening of the bladder 310 and is secured by the shrink tubing 920.

In some embodiments, a female-to-male connector is used to connect the bladder to the tube assembly 130-5. The female end of the connector is sized to snugly fit over the end portion of the tube assembly 130-5. The male end of the connector is sized to snugly fit inside the opening of the bladder 310. The shrink tubing 920 is wrapped over the opening of the bladder 310, the female-to-male connector, and the end of the tube assembly 130-5. Other types of connectors, such as male-to-male connector, female-to-female connector, male-to-female connector for creating an interference fit and/or a screw connection with the tube assembly 130-5 and the bladder 310 can be used.

Figure 11A:
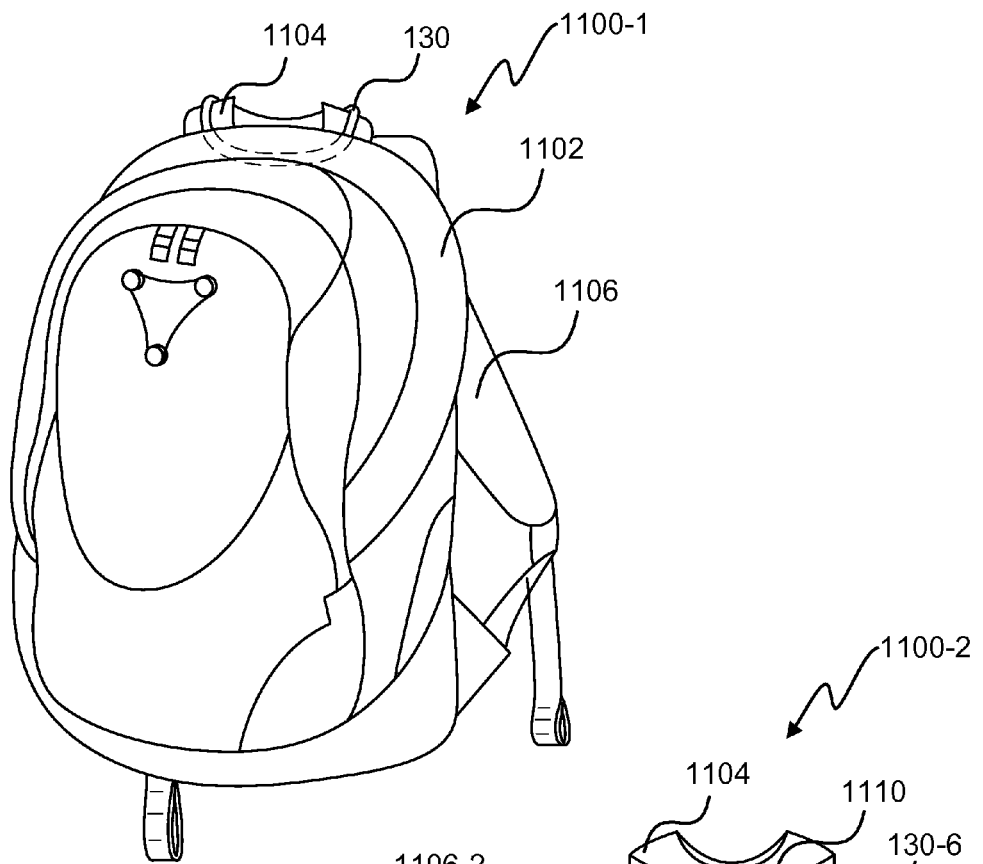
FIGS. 11A-11B illustrate views of embodiments of a carrying device for housing the liquid encapsulating device.

With reference to FIG. 11A, an embodiment of a carrying device, bag or a backpack 1100-1 for accommodating the tube assembly 130 is shown. The backpack 1100-1 include one or more compartments 1102 for receiving items, a carry handle 1104, and two shoulder straps 1106. One of the compartment 1102 include two openings formed near the carry handle 1104. A portion of the tube assembly 130 is received inside the compartment 1102. The two ends of the tube assembly 130 are thread through the two openings of the compartment 1102 and are positioned outside the compartment 1102. In some embodiments, the openings of the compartment 1102 are each reinforced by the reinforcements 500 similar to those described above with reference to FIGS. 5-8. The reinforcements 500 guides the tube assembly to extend towards the back of the backpack 1100-1. Therefore, when a user carries the backpack 1100-1 on the user's back using one or both of the shoulder straps 1106, the portions of the tube assembly 130 outside the compartment 1102 extend around the user's neck and over the shoulders of the user.

Figure 11B:
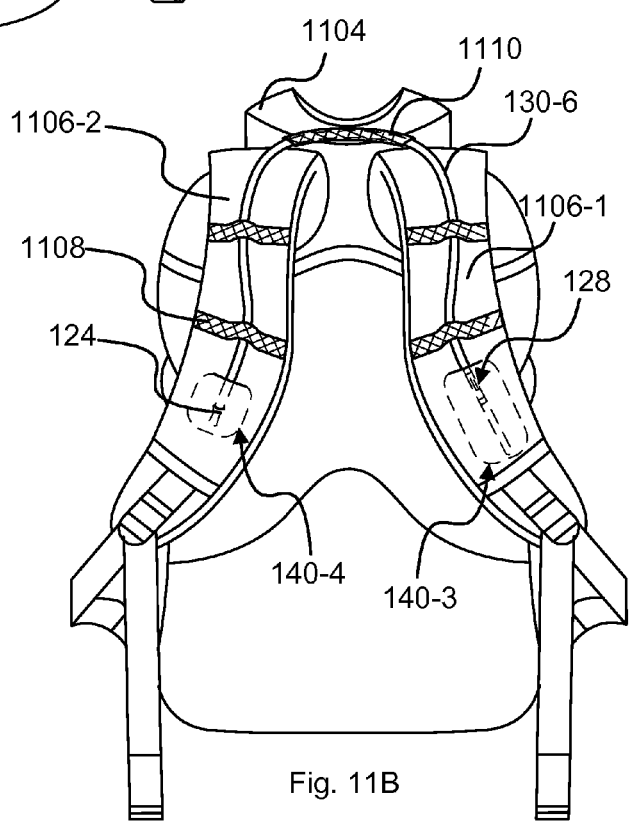

With reference to FIG. 11B, an alternative embodiment of a carrying device, a bag or a backpack 1100-2 for accommodating the tube assembly 130-6 is shown. In this embodiment, the tube assembly 130-6 is removable attached to the shoulder straps 1106. The backpack 1100-2 further includes pockets 140 on the shoulder straps 1106 for receiving the mouthpiece 124 and the vaporizing device 128.

The shoulder straps 1106 each include one or more securing webbings or securing tapes 1108. The ends of each securing tape 1108 are joined to the shoulder strap 1106 by sewing, adhering, stapling, hook-and-loop fastener, or any other suitable connection mechanisms. The middle portion of the securing tape 1108 is not joined to the shoulder strap 1106 and thus defines a passage for threading through the tube assembly 130-6. To facilitate threading through the securing tapes 1108, the tube assembly 130-6 is a single layer tube and does not include the fabric or cloth tube outer layer 220 in one embodiment. In some embodiments, the securing tapes 1108 are formed as securing loops or rings. The securing tapes 1108 can be made of fabric, leather, plastic, natural or synthetic materials, woven or non-woven materials, webbings, elastic bands, or any suitable materials.

In the embodiment shown in FIG. 11B, the middle portion of the tube assembly 130-6 includes a tube outer segment 1110 that is made of fabric, leather, or any suitable material. As such, when the tube assembly 130-6 rests on the user's neck, the tube outer segment 1110 limits and/or prevent any discomfort the user may feel. In some embodiments, the tube outer segment 1110 is further removably attached to the carry handle 1104 or is simply thread through the carry handle 1104.

With further reference to FIG. 11B, the shoulder straps 1106 include pockets 140 similar to those described above with reference to FIGS. 1B-1D. In this embodiment, the left shoulder strap 1106-1 includes a left strap pocket 140-3 for receiving the vaporizing device 128, and the right shoulder strap 1106-2 includes a right strap pocket 140-4 for receiving the mouthpiece 124. Although the pockets 140 are formed of different sizes in this embodiment, the pockets 140 can be formed of the same size in other embodiments.

Figure 12:
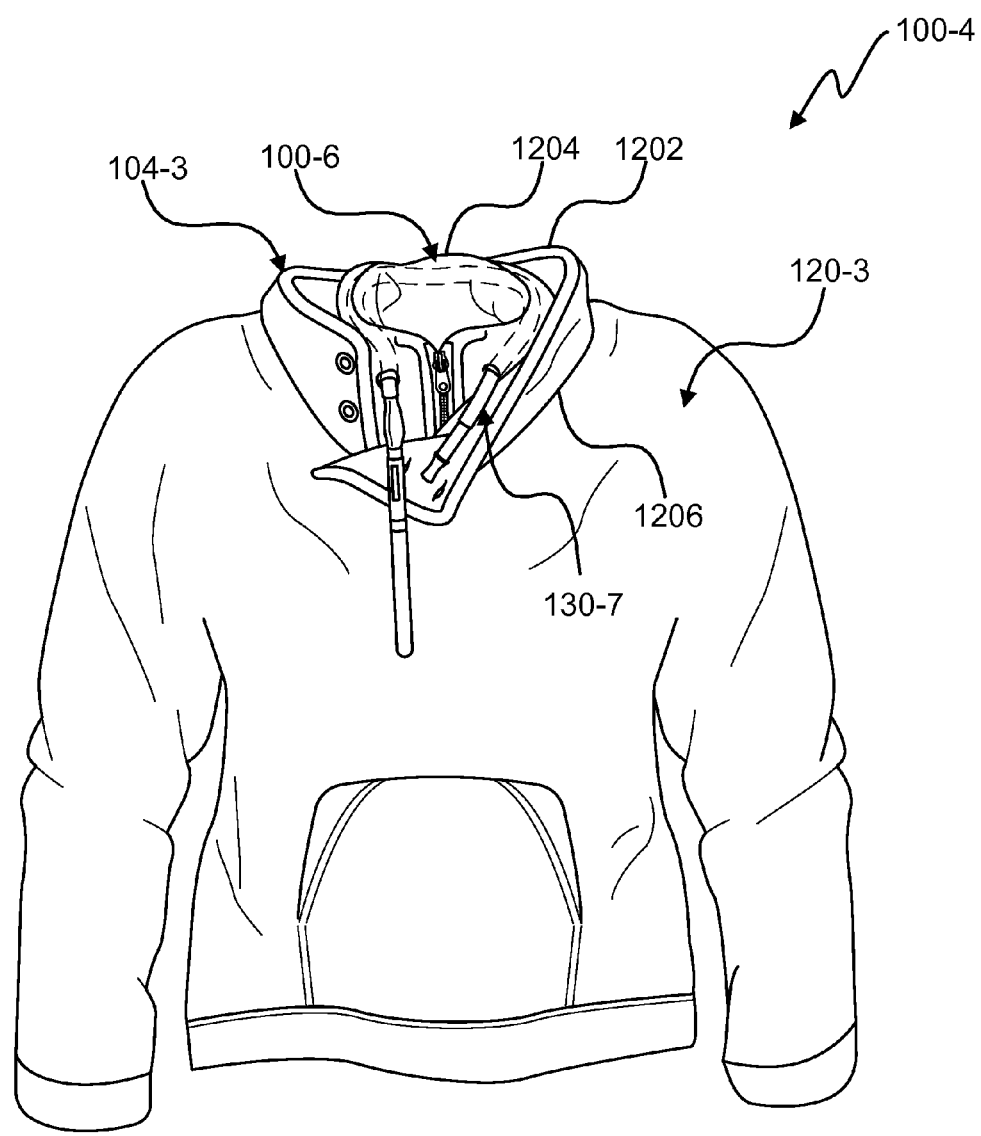
FIG. 12 illustrates a front view of an embodiment of another body-top garment for housing the liquid encapsulating device.

With reference to FIG. 12, another embodiment of a clothing top, body-top garment or sweatshirt 100-4 for accommodating various technologies is shown. The sweatshirt 100-4 includes an above-shoulder element or collar system 104-3 that is attached to a garment body 120-3. The collar system 104-3 include an inner collar 1202 and an outer collar 1204. Both the inner collar 1202 and the outer collar 1204 are stand-up collars and are attached to the garment body 120-3 through a common stitch 1206.

In some embodiments, the inner collar 1202 has a double-layer structure. The two layers of the inner collar 1202 forms an elongated pouch 110-6 that is similar to the elongated pouches 110 described above. In some embodiments, the inner collar 1202 is similar to the collar 104 described above with reference to FIGS. 3A-4. Although in this embodiment, only the inner collar 1202 includes the elongated pouch 110-6, the outer collar 1204 could also includes the elongated pouch 110 similar to any of the elongated pouches 110 described above. In some embodiments, only the outer collar 1202 includes the elongated pouch 110. In some embodiments, the inner collar 1202 is part of another sweatshirt 100 that can be worn independently.

Figure 13:
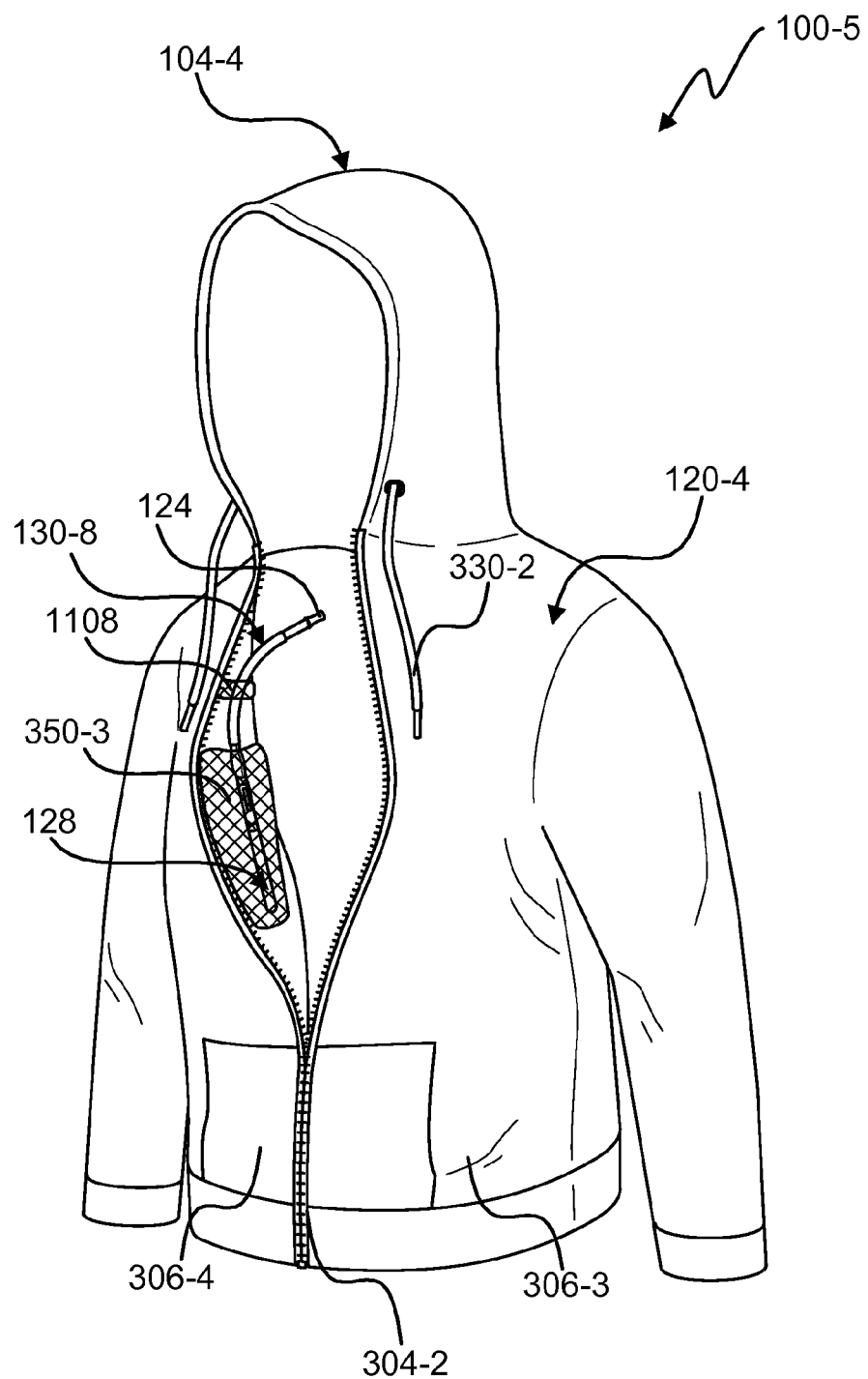
FIG. 13 illustrates a perspective view of an embodiment of yet another body-top garment for housing the liquid encapsulating device.

With reference to FIG. 13, another embodiment of a clothing top, body-top garment or sweatshirt 100-5 for accommodating various technologies is shown. In this embodiment, the sweatshirt 100-5 includes a hood 104-4 attached to a garment body 120-4. The hood 104-4 includes a drawstring 330-2 for tightening the hood 104-4 around the head of the wearer. The garment body 120-4 includes a front zipper 304-2 that divides the front of the sweatshirt 100-5 into a left half 306-3 and a right half 306-4.

The sweatshirt 100-5 further includes a left inner pocket 350-3 positioned on the interior of the right half 306-4 and a securing tape 1108 above the inner pocket 350-3. The left inner pocket 350-3 and the securing tape 1108 cooperate to accommodate various technologies. In some embodiments, the left half 306-3 further includes a left inner pocket and a cooperating securing tape for accommodating a second technology. In other embodiments, the hood 104-4 is further configured with the elongated pouch 110 similar to those described above with reference to FIGS. 1A-2 to accommodate a third technology.

In the embodiment shown in FIG. 13, the left inner pocket 350-3 receives the vaporizing device 128 that is attached to an end of a tube assembly 130-8. The tube assembly 130-8 is similar to the tube assemblies 130 described above, but shorter. The tube assembly 130-8 is thread through the securing tape 1108 and held in place by the securing tape 1108. The other end of the tube assembly 130-8 points generally upward. The mouthpiece 124 attached to the other end of the tube assembly 130-8 is below the mouth and/or the neck of the wearer. This way, the mouthpiece 124 and the tube assembly 130-8 attached thereto are concealed inside the sweatshirt 100-5.

When the wear desires to consume the fluidal or vaporized material, the mouthpiece 124 is pulled up by the wearer to the wearer's mouth. The right inner pocket 350-3 and the securing tape 1108 are made of materials (such as a lining or netting material) that allow the vaporizing device 128 and the tube assembly 130-8 to slide up and down easily. Other suitable materials includes, but not limited to, fabric, plastic, leather, natural or synthetic materials, and/or woven or non-woven materials.

Figure 14:
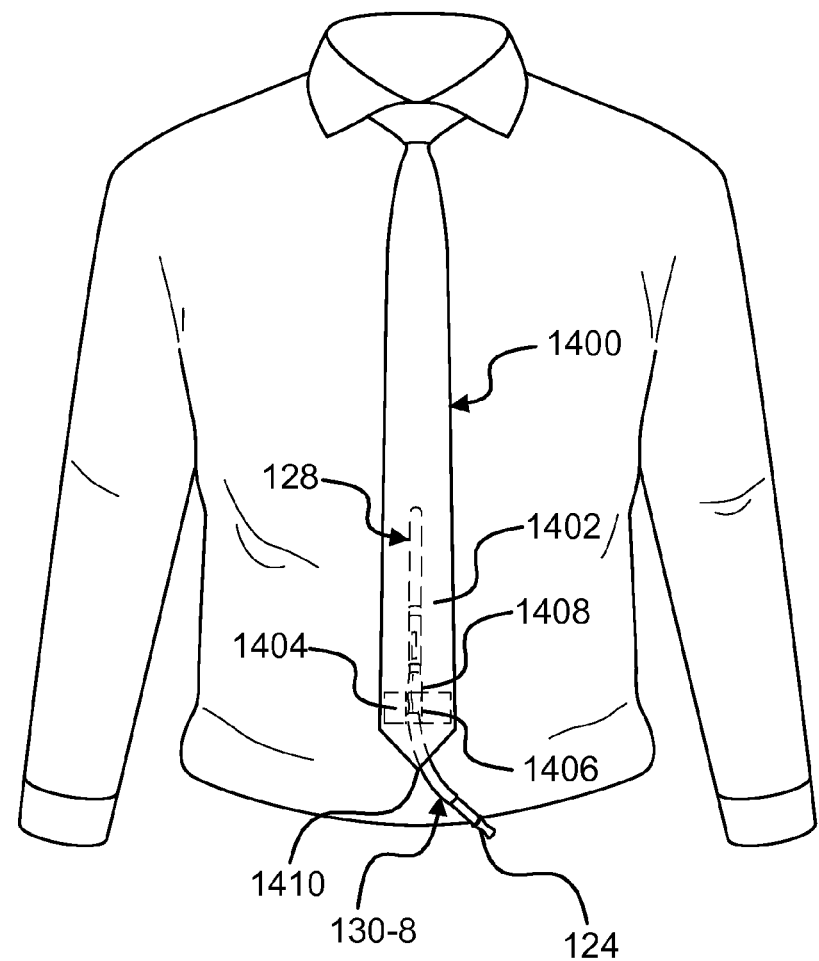
FIGS. 14-16 illustrate views of various embodiments of a wearable accessory for housing the liquid encapsulating device.

With reference to FIG. 14, an embodiment of a wearable accessory, body-top accessory, wearable accessory, or tie 1400 for accommodating various technologies is shown. While a body-top garment or a shirt is also shown, the tie 1400 can be worn and/or used by the wearer with or without the shirt. The tube assembly 130-8 similar to that described above with reference to FIG. 13 is secured to the back of a wider end or head 1402 of the tie 1400 by a securing strap 1404. The vaporizing device 128 attached to one end of the tube assembly 130-8 is received inside a sleeve formed by the front and back layers of the head 1402. The mouthpiece 124 extends beyond a tip 1410 of the tie 1400.

The securing strap 1404 is joined to the head 1402 such that a channel 1406 for passing through the tube assembly 130-8 is formed between the securing strap 1404 and the head 1402. The channel 1406 has a width allows the tube assembly 130-8 and the mouthpiece 124 to slide through but prevents the vaporizing device 128 to slide through. In some embodiments, the end of the channel 1406 that is closer to the tip 1410 has a smaller width than that of the end further away from the tip 1410 to further limit the downward movement of the vaporizing device 128.

In some embodiments, the joint between the tube assembly 130-8 and the vaporizing device 128 is wrapped around by one or more of shrink tubing, rubber rings, tapes, and/or other layered or tubular members to form an enlarged portion 1408. The enlarged portion 1408 prevents the vaporizing device 128 from sliding into and/or through the channel 1406.

In this embodiment, the mouthpiece 124 and a portion of the tube assembly 130-8 extends beyond the tip 1410 of the tie 1400. In some embodiments, the securing strap 1404 is positioned higher up and further away from the tip 1410 and/or the tube assembly 130-8 is shorter so that the mouthpiece 124 and the tube assembly 130-8 are hidden from view. In some embodiments, the securing strap 1404 is joined to a narrower end or tail of the tie 1400. In other embodiments, both the head 1402 and the tail include the securing straps 1404 for accommodating two technologies.

Figure 15:
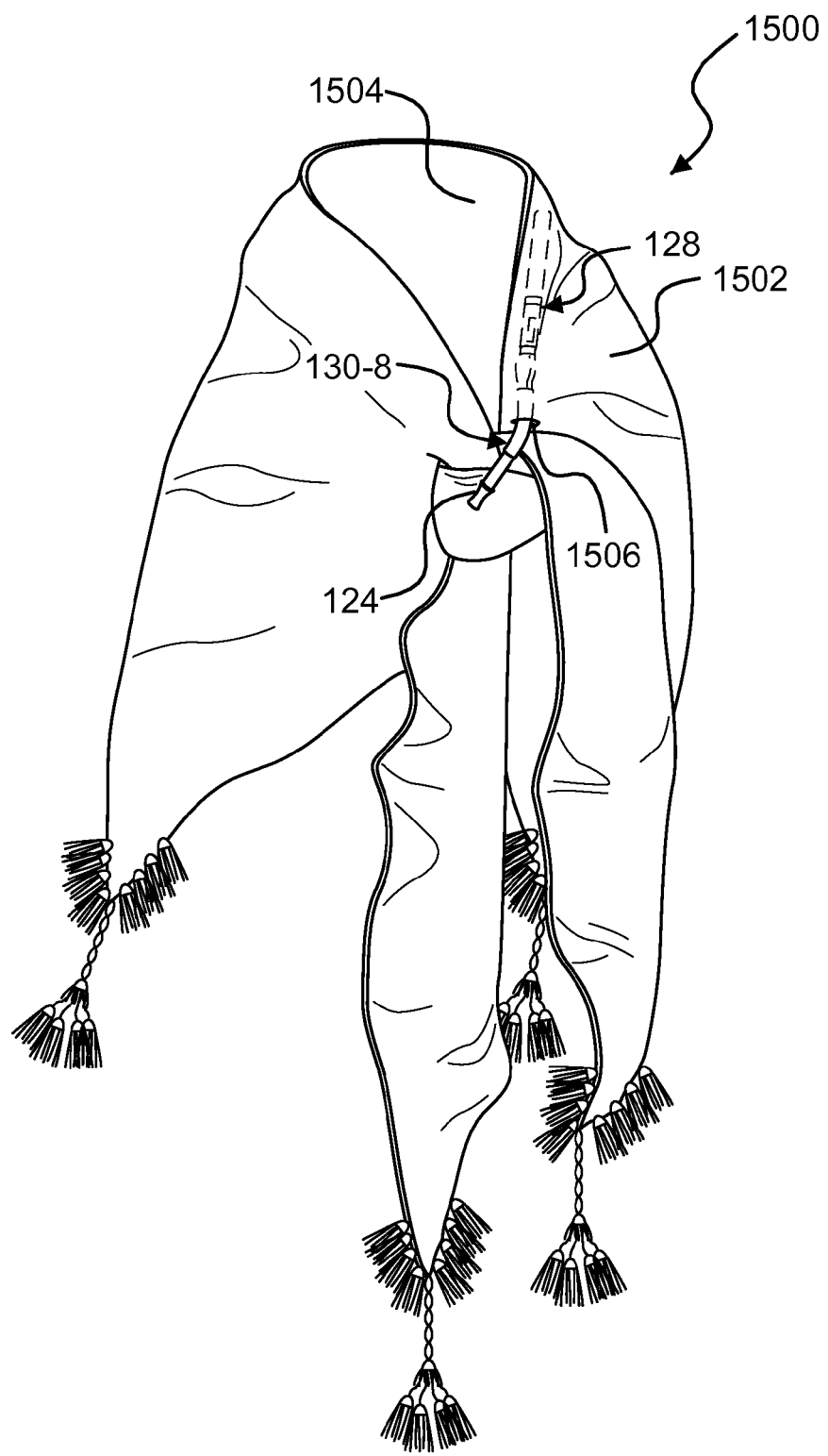

With reference to FIG. 15, an embodiment of a wearable accessory, body-top accessory or shawl 1500 for accommodating various technologies is shown. The shawl 1500 can be worn on the shoulder and/or around the neck of the wearer. In this embodiment, the shawl 1500 is wrapped around the wearer's shoulder and neck and is tied at the front. The shawl 1500 includes an exterior layer 1502 and an interior layer 1504. An elastic opening 1506 is formed on the exterior layer 1502. The vaporizing device 128 and the adjoining portion of the tube assembly 130-8 are thread through the elastic opening 1506 into a space defined by the exterior layer 1502 and the interior layer 1504. In some embodiments, stitches, seams and/or tapes are used to compartmentalize the space and to hold the vaporizing device 128 in place.

In its natural state, the elastic opening 1506 has a diameter smaller than the outer diameter of the tube assembly 130-8, the outer diameter of the vaporizing device 128 and/or the diameter of the joint between the tube assembly 130-8 and the vaporizing device 128. As such, the vaporizing device 128 and/or the tube assembly 130-8 do not fall from and/or slide freely through the elastic opening 1506.

In some embodiments, the elastic opening 1506 is located on the interior layer 1504, instead of the exterior layer 1502. The mouthpiece 124 and/or the adjoining portion of the tube assembly 130-8 extend outside the interior layer 1504 of the shawl 1500. When the shawl 1500 is worn by the wearer, the mouthpiece 124 and/or the adjoining portion of the tube assembly 130-8 are hidden from view. In some embodiments, both the exterior layer 1502 and the interior layer 1504 are formed with one or more elastic openings 1506 to accommodate multiple technologies. While FIG. 15 shows the elastic opening 1506 is positioned near the left shoulder of the wearer, the elastic opening 1506 is formed near the right shoulder of the wearer in other embodiments.

Figure 16:
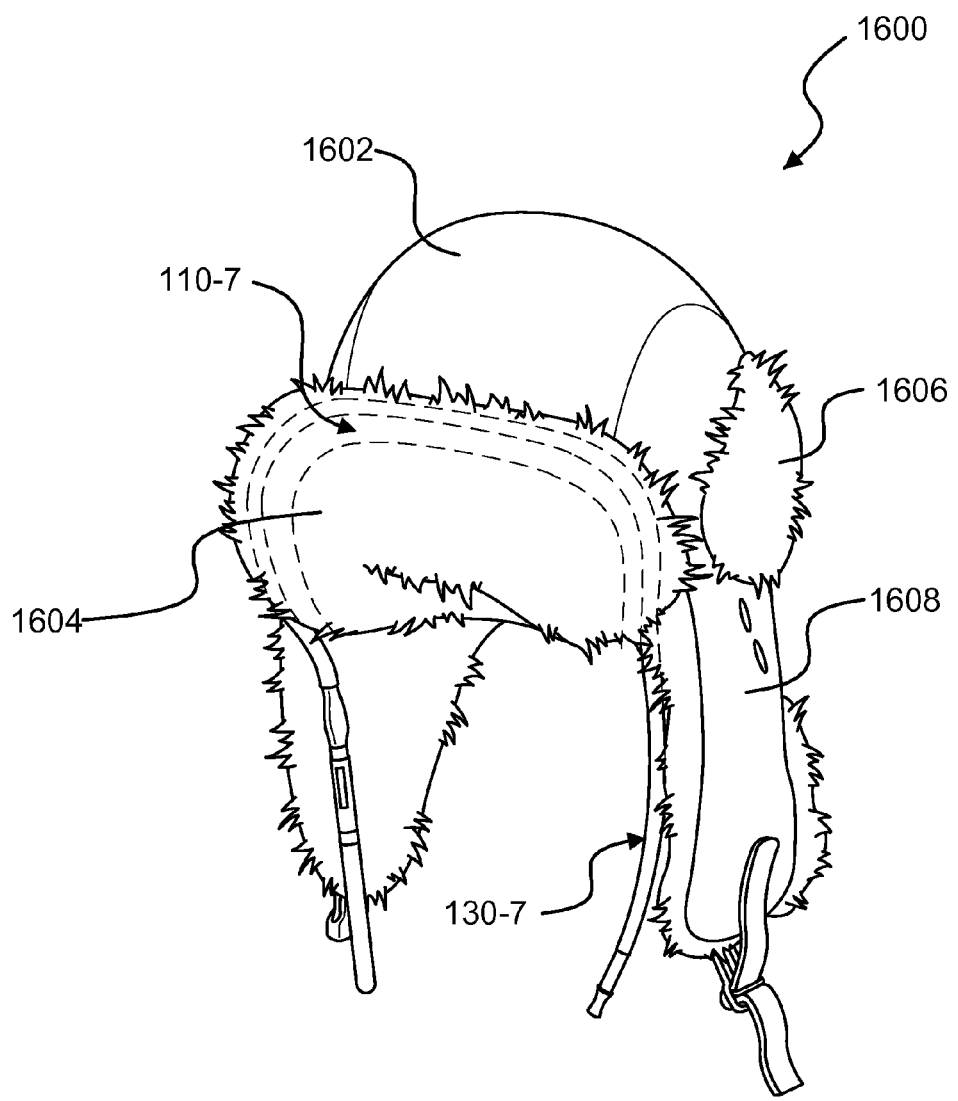

Although a double-layer shawl 1500 is described, the shawl 1500 can be a single layer shawl formed with the elastic opening 1506 and/or the securing strap 1404 described above with reference to FIG. 14. The exterior and interior layers 1502, 1504 may be made of the same or different materials, such as fabric, leather, plastic, natural or synthetic materials, woven or non-woven materials, and/or any other suitable materials. The exterior layer 1502 and/or the interior layers 1504 can be further treated to protect the wearer from various weather elements and/or treated for fire proofing With reference to FIG. 16, an embodiment of a wearable accessory, over-the-head accessory, head covering, or hat 1600 for accommodating various technologies is shown. The tube assembly 130-7 described above with reference to FIG. 11 is removably attached to the hat 1600. The hat 1600 includes: a over-the-head covering or crown 1602, a front member or front brim 1604 extending from a front edge of the crown 1602, a back member 1606 extending from a back edge of the crown 1602, and side members, ear coverings or ear flaps 1608 extending from side edges of the crown 1602. The ear flaps 1608 can be releasably joined to each other over the crown 1602 or under the chin of the wearer.

The front brim 1604 projects forward and/or upward. In some embodiments, the front brim 1604 can be folded towards the crown 1602 to rest against the crown 1602. The front brim 1604 include an elongated pouch 110-7 similar to the elongated pouches 110 described above. The elongated pouch 110-7 is positioned on the upper surface of the front brim 1604 in this embodiment, but could be positioned on the lower surface of the front brim 1604 in other embodiments. In some embodiments, the elongated pouch 110-7 includes the embedded zipper 114 or the exposed zipper 116 for easy removal of the tube assembly 130-7. The embedded zipper 114 or the exposed zipper 116 is positioned along portions of the leading and/or side peripheries of the front brim 1604.

The elongated pouch 110-7 traverses along the leading and/or side peripheries of the front brim 1604. Openings for threading the tube assembly 130-7 into and out of the elongated pouch 110-7 are positioned along the side peripheries of the front brim 1604. Accordingly, when the front brim 1604 projects forward and/or upward, or when the front brim 1604 is folded toward the crown 1602, the tube assembly 130-7 extends downward from the front brim 1604. In some embodiments, the elongated pouch 110-7 is defined by the space between the two layers of material (e.g. an upper layer material and a lower layer material) forming the front brim 1604. As such, the tube assembly 130-7 can be positioned along the peripheries of the front brim 1604, close to the crown 1602, or anywhere inbetween.

In some embodiments, the ear flaps 1608, the back member 1606 also includes the elongated pouch 110-7 positioned along portions of the periphery of the back member 1606 for accommodating a second technology. In some embodiments, the interior surfaces of the ear flaps 1608 further have pockets 140, securing straps 1404 and/or securing tapes 1108 for receiving and/or securing the vaporizing device 128, the mouthpiece 124, and/or portions of the tube assembly 130-7. In some embodiments, the elongated pouch 110 is positioned on the crown 1602 and traverses around and/or over the crown 1602.

In some embodiments, the hat 1600 only includes the front brim 1604 and does not include the back member 1606 or the ear flaps 1608. Although a hat is shown, the elongated pouch 130-7 can also be incorporated into the front brim of a visor, a helmet or any head covering. In some embodiments, the hat 1600 includes a full brim that traverses around the entire periphery of the crown 1602. The tube assembly 130 traverses around or over of the crown 1602 and thread through openings formed in the hat 1600 to fall along either side of the wearer's head.

Figure 17:
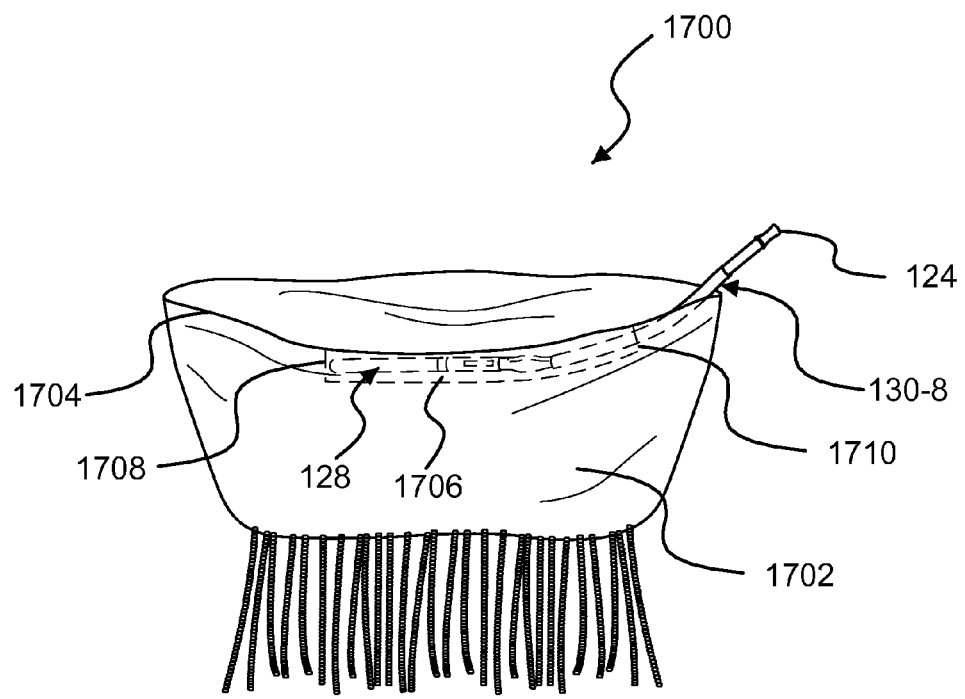
FIGS. 17-19 illustrate views of various embodiments of a carrying accessory for housing the liquid encapsulating device.

With reference to FIG. 17, an embodiment of a carrying accessory, handbag, bag, clutch bag, or purse 1700 for accommodating various technologies is shown. The purse 1700 includes a compartment body 1702 having one or more compartments for receiving items. The upper rim 1704 of the compartment body 1702 defines an opening for accessing the one or more compartments.

An elongated sleeve 1706 is positioned inside the compartment body 1702 along a portion of the upper rim 1704. The elongated sleeve 1706 includes a closed end 1708 and an open end 1710. The vaporizing device 128 and the adjacent portion of the tube assembly 130-8 are slid into the elongated sleeve 1706 from the open end 1710. The mouthpiece 124 and the adjacent portion of the tube assembly 130-8 extends outside the elongated sleeve and/or the compartment body 1702. In some embodiments, while the mouthpiece 124 and the tube assembly 130-8 extend outside the elongated sleeve 1706, they are still contained inside the compartment body 1702.

Figure 18:
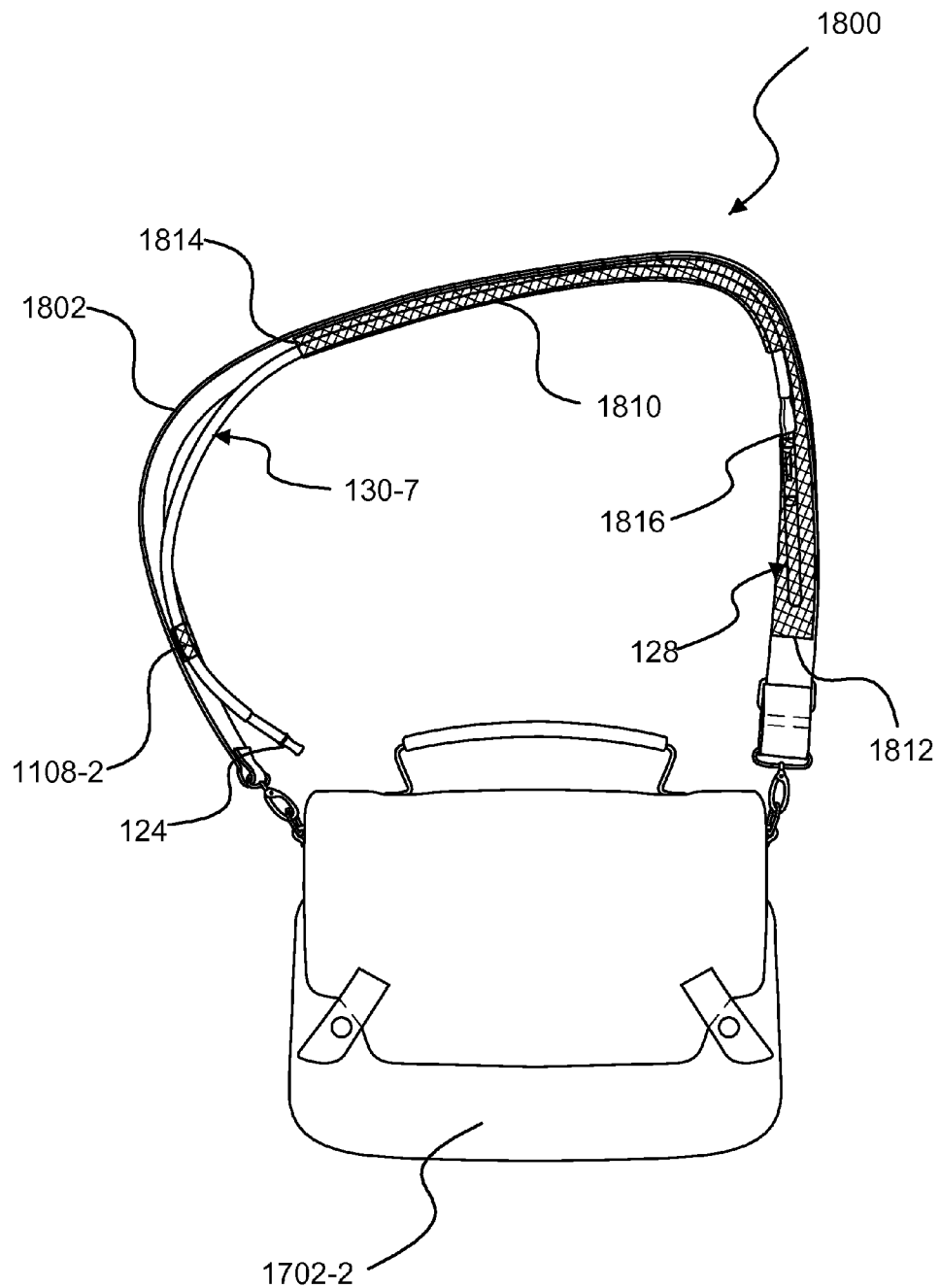

With reference to FIG. 18, an embodiment of a carrying accessory, handbag, bag, or messenger bag 1800 for accommodating various technologies is shown. The messenger bag 1800 includes a compartment body 1702-2 and an adjustable strap 1802. The adjustable strap 1802 is releasably attached to the sides of the compartment body 1702-2.

The adjustable strap 1802 include an adjustable-strap sleeve 1810 that traverses about 70% of the adjustable strap 1802 in this embodiment, but could traverse no less than 30%, 40%, 50%, 60%, 80%, or 90% of the adjustable strap 1802. The adjustable-strap sleeve 1810 has a pocket end 1812, an insertion end 1814 and a window 1816. The pocket end 1812 is closed and is positioned near one end of the adjustable strap 1802. The vaporizing device 128 and the tube assembly 130-7 are inserted through the insertion end 1814 into the adjustable-strap sleeve 1810. The window 1816 is for activating, deactivating, and/or replacing the vaporizing device 128 without removing the tube assembly 130-7 from the adjustable-strap sleeve 1810. The adjustable strap 1802 further includes one or more securing tape 1108-2 positioned near the other end of the adjustable strap 1802. The securing tape 1108-2 secures the mouthpiece 124 and/or the tube assembly 130-7 to the adjustable strap 1802.

Figure 19:
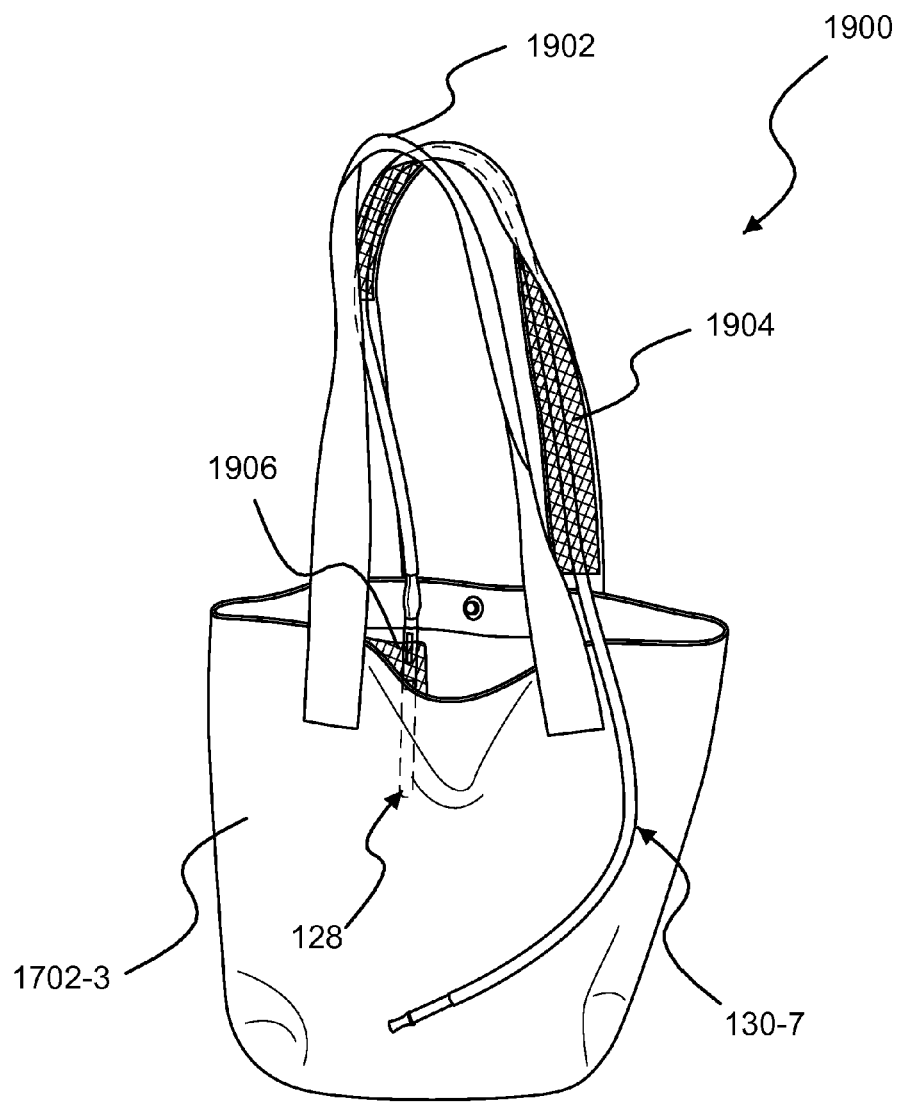

With reference to FIG. 19, an embodiment of a carrying accessory, handbag, bag, or tote 1900 for accommodating various technologies is shown. The tote 1900 includes a compartment body 1702-3 and a pair of carrying straps 1902. One of the carrying straps 1902 includes a carrying-strap sleeve 1904 positioned on one side the carrying strap 1902 facing the other carrying strap 1902. Both ends of the sleeve 1902 are open for threading the tube assembly 130-7. The vaporizing device 128 is received in a compartment pocket 1906 positioned inside the compartment body 1702-3. The compartment pocket 1906 is positioned along the extension of the carrying strap 1902 such that the tube assembly 130-7 extend along the carrying strap 1902.

The carrying-strap sleeve 1904 traverses at least a middle portion of the carrying strap 1902. As such, the portions of the tube assembly 130-7 that are outside the carrying-strap sleeve 1904 points toward the compartment body 1702-3. The carrying-strap sleeve 1904 traverses no less than 30%, 40%, 50%, 60%, 70%, 80% or 90% in various embodiments. In some embodiments, the carrying-strap sleeve 1904 traverses the entire carrying strap 1902. Although only one carrying strap 1902 has the carrying-strap sleeve 1904 in this embodiment, both carrying straps 1902 each have the carrying-strap sleeve 1904 in other embodiments to accommodate multiple technologies.

Figure 20:
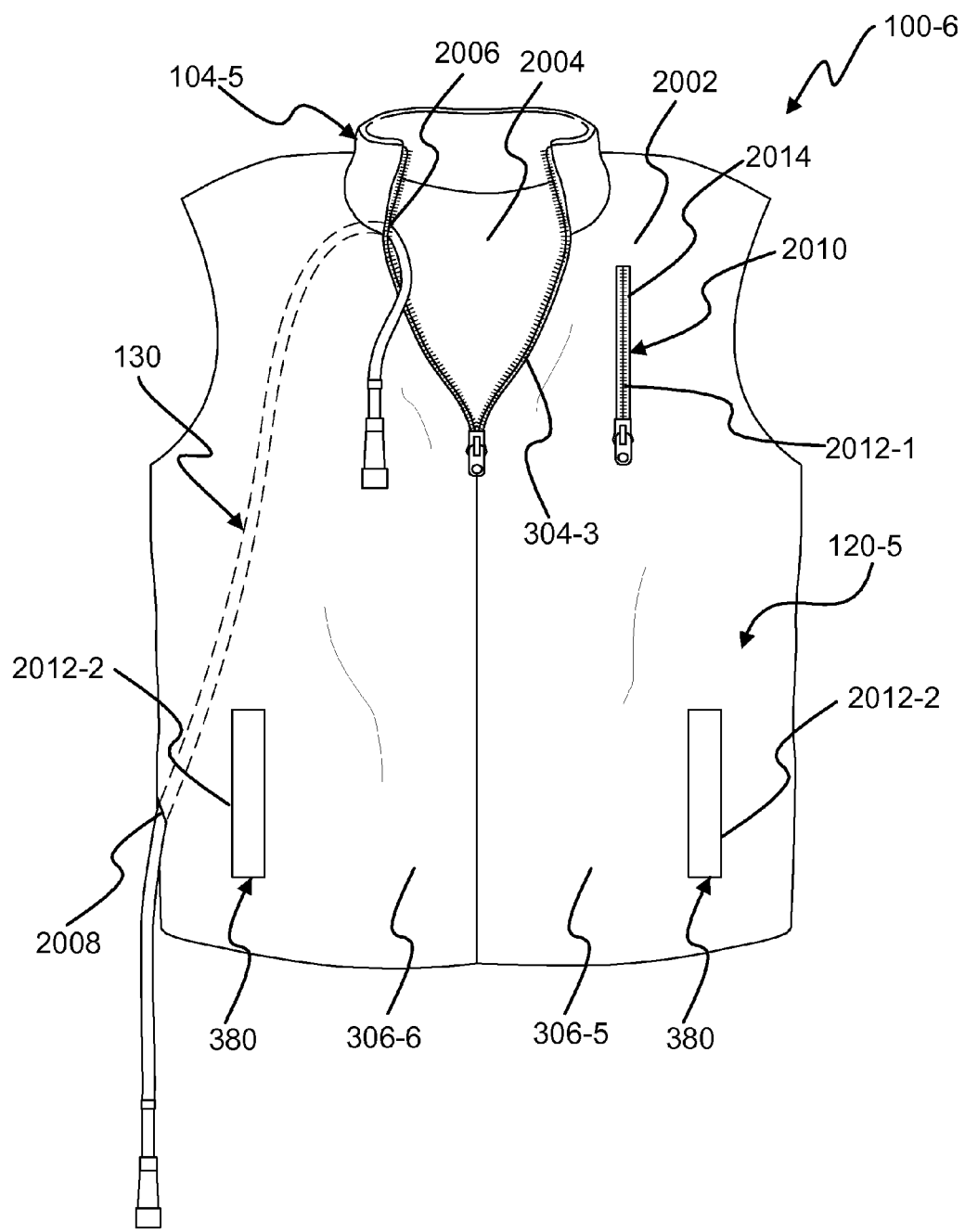
FIG. 20 illustrates a front view of an embodiment of another body-top garment for housing the liquid encapsulating device.

With reference to FIG. 20, another embodiment of a clothing top, body-top garment or vest 100-6 for accommodating various technologies is shown. The vest 100-6 includes an above-shoulder element or collar 104-5 that is attached a sleeveless garment body 120-5. The garment body 120-5 includes a vest exterior layer 2002 and a vest interior layer 2004. The garment body 120-5 further includes a front zipper 304-3 that divides the front of the vest 100-6 into a left half 306-5 and a right half 306-6.

The garment body 120-5 includes a chest pocket 2010 and two hand pockets 380. The chest pocket 2010 includes a chest pouch (not shown) and a side opening 2012-1 for accessing the chest pocket 2010. Each of the hand pockets 380 includes a hand pouch (not shown) and a side opening 2012-2 for accessing the hand pouch. The side openings 2012 are oriented substantially vertically in this embodiment, but can be oriented slanted, diagonally, obliquely, or horizontally. In some embodiments, one or more of the side openings 2012 can have a curved profile. One or more of the side openings 2012 can be closed by a zipper 2014, hook-and-loop fasteners or snap buttons.

The right half 306-6 includes an upper opening 2006 positioned on the vest interior layer 2004 and a lower opening 2008 positioned on the vest exterior layer 2002. In some embodiments, the upper opening 2006 is also positioned on the vest exterior layer 2002. In some embodiments, the upper opening 2006 and/or the lower opening 2006 is formed by leaving an opening along the seam joining the pieces of materials forming the vest 100-6. For example, the upper opening 2006 is formed at the seam joining the zipper 304-3, the vest interior layer 2004, and/or the vest exterior layer 2002 near the collar 104-5. The lower opening 2008 is formed at the seam joining the front and back vest exterior layers 2004.

A tube assembly 130 similar to that described above with reference to FIG. 9K is thread through the upper opening 2006 and the lower opening 2008 and a portion of the tube assembly 130 is received inside the space defined and/or enclosed by the vest exterior layer 2002 and the vest interior layer 2004. In this embodiment, the upper opening 2006 is positioned near the collar 104-5 and/or the zipper 304-3, and the lower opening 2008 is positioned on the side of the vest. In some embodiments, the left half 306-5 also includes the upper opening 2006 and the lower opening 2008 for housing another tube assembly 130.

The lower opening 2008 is further positioned near the hand pocket 380 such that the technology attached to the lower end of the tube assembly 130 can be received inside the hand pocket 380. The upper end of the tube assembly 130 and the mouth piece 124 attached to the upper end can be received inside the chest pocket 2010. In some embodiments, the vest 100-6 includes an internal chest pocket such that the mouth piece 124 attached to the upper end of the tube assembly 130 can be received inside the internal chest pocket.

Specific details are given in the above description to provide a thorough understanding of the embodiments. However, it is understood that the embodiments may be practiced without these specific details.

While the principles of the disclosure have been described above in connection with specific apparatuses and methods, it is to be clearly understood that this description is made only by way of example and not as limitation on the scope of the disclosure.

What is claimed is:

1. A body-top garment for removably housing various technology, the body-top garment comprising:
    an above-the-shoulder element, comprising:
        a head opening, configured to extend around at least part of a neck and/or head of a wearer;
        an elongated pouch traversing around at least a portion of the head opening, the elongated pouch comprising:
            a left end,
            a right end, and
            an opening,
        a zipper that selectively closes the opening,
        a left opening of the left end of the elongated pouch, wherein:
            the left opening has a first reinforcement around the left opening, and
            the left opening has a first dimension across the left opening;
        a right opening of the right end of the elongated pouch, wherein:
            the right opening has a second reinforcement around the right opening, and
            the right opening has a second dimension across the right opening;
    a garment body below the shoulder line, comprising:
        a pocket accessible to the wearer, the pocket comprising:
            a pouch, and
            a horizontal opening; and
    a tube
        sized to traverse the elongated pouch and pass through the right opening and left opening, and
        the tube configured to pass from outside the right opening to outside the left opening,
        wherein:
            the horizontal opening is positioned to meet at least part of the tube, and
            sized to pass the at least part of the tube into the pouch.

2. The body-top garment for removably housing various technology of claim 1, wherein the zipper is at least partially concealed by a flap.

3. The body-top garment for removably housing various technology of claim 1, wherein the reinforcement comprises a grommet with a shape.

4. The body-top garment for removably housing various technology of claim 3, wherein the shape of the grommet is selected from circle, oval, triangle, square, rectangle, and/or diamond.

5. The body-top garment for removably housing various technology of claim 1, further comprising:
    a compartment; and
    a drawstring traversing the compartment, wherein the drawstring is configured to tighten at least a portion of the head opening.

6. The body-top garment for removably housing various technology of claim 1, wherein the elongated pouch has a length of 10 inches or more.

7. The body-top garment for removably housing various technology of claim 1, wherein the first dimension and the second dimension are at least one centimeter to accommodate the tube.

8. The body-top garment for removably housing various technology of claim 1, further comprising a mouthpiece connected to a first end of the tube and a liquid encapsulating device connected to a second end of the tube, wherein the mouthpiece and the liquid encapsulating device are outside the elongated pouch.

9. The body-top garment for removably housing various technology of claim 8, wherein the mouthpiece is connected to an interior of the tube using an interference fit.

10. The body-top garment for removably housing various technology of claim 8, wherein:
the mouthpiece uses a first adapter to connect to a first end of the tube, and
the liquid encapsulating device uses a second adapter to connect to a second end of the tube, wherein the first adapter is threaded opposite to the second adapter such that they could be screwed together.

11. The body-top garment for removably housing various technology of claim 8, wherein the liquid encapsulating device further comprises a vapor chamber, a battery, an activation switch, and a vapor outlet.

12. The body-top garment for removably housing various technology of claim 8, wherein the liquid encapsulating device fits through the second opening.

13. A body-top garment for removably housing various technology, the body-top garment comprising:
an above-the-shoulder element, comprising:
an elongated pouch comprising a left end and a right end;
a continuous area; and
the continuous area extending from the left end to the right end wherein the area is openable and closeable;
a left opening of the left end of the elongated pouch, wherein:
the left opening has a first reinforcement around the left opening, and
the left opening has a first dimension across the left opening of at least one centimeter;
a right opening of the right end of the elongated pouch, wherein:
the right opening has a second reinforcement around the right opening, and
the right opening has a second dimension across the right opening;
a tube
sized to traverse the elongated pouch and pass through the right opening and left opening, and
the tube configured to pass from outside the right opening to outside the left opening.

14. The body-top garment for removably housing various technology of claim 13, further comprising: a vapor apparatus;
a pocket accessible to the wearer, comprising:
a pouch, wherein the pouch is configured to encapsulated at least part of the vapor apparatus, and
a horizontal opening sized to pass the at least part of the vapor apparatus into the pouch.

15. The body-top garment for removably housing various technology of claim 13, further comprising a second reinforcement wherein the right opening has the second reinforcement around the right opening having a second dimension across the right opening of at least one centimeter.

16. A body-top garment for removably housing various technology, the body-top garment comprising:
a left opening has a first reinforcement around the left opening, and
the left opening has a first dimension across the left opening;
a right opening has a second reinforcement around the right opening, and
the right opening has a second dimension across the right opening;
a tube
sized to pass through the left opening and right opening, and
configured to pass from outside the right opening to outside the left opening; and
a pocket accessible to the wearer, the pocket comprising:
a pouch comprising: a continuous area; and the continuous area extending from the left opening to the right opening wherein the continuous area is openable and closeable; and
a horizontal opening; wherein:
the horizontal opening is:
positioned to meet at least part of the tube, and
sized to pass the at least part of the tube into the pouch.

17. The body-top garment for removably housing various technology of claim 16, further comprising:
an above-the-shoulder element, comprising:
a head opening, configured to extend around at least part of a neck and/or head of a wearer;
an elongated pouch traversing at least a portion of the head opening, the elongated pouch having:
a left end,
a right end, and
an opening, and
a zipper that opens and closes the opening.

18. The body-top garment for removably housing various technology of claim 16, further comprising:
a tube:
sized to traverse the elongated pouch and pass through the right opening and left opening, and
configured to pass material from outside the right opening to outside the left opening.

19. The body-top garment for removably housing various technology of claim 16, further comprising a liquid encapsulating device, wherein the liquid encapsulating device fits through the right opening.

* * * * *